US006365591B1

(12) United States Patent
Leonardi et al.

(10) Patent No.: US 6,365,591 B1
(45) Date of Patent: Apr. 2, 2002

(54) ISOXAZOLECARBOXAMIDE DERIVATIVES

(75) Inventors: Amedeo Leonardi, Milan; Gianni Motta, Barlassina; Carlo Riva, Varese; Elena Poggesi, Milan, all of (IT)

(73) Assignee: Recordati, S.A., Chemical and Pharmacueticals Company, Chiasso (CH)

( * ) Notice: Subject to any disclaimer, the term of this patent is extended or adjusted under 35 U.S.C. 154(b) by 0 days.

(21) Appl. No.: 09/691,778

(22) Filed: Oct. 18, 2000

Related U.S. Application Data
(60) Provisional application No. 60/218,314, filed on Jul. 14, 2000.

(30) Foreign Application Priority Data

Oct. 18, 1999 (IT) .......................................... MI99A2173

(51) Int. Cl.[7] ...................... C07D 413/12; A61K 31/422
(52) U.S. Cl. .................................. 514/254.04; 544/367
(58) Field of Search ...................... 514/254.04; 544/367

(56) References Cited

U.S. PATENT DOCUMENTS

| | | | |
|---|---|---|---|
| 4,089,969 A | 5/1978 | Muchowski et al. | 424/274 |
| 5,091,182 A | 2/1992 | Ong et al. | 424/400 |
| 5,317,020 A | 5/1994 | Emonds-Alt et al. | 514/255 |
| 5,358,948 A | 10/1994 | Bradshaw et al. | 514/252 |
| 5,403,842 A * | 4/1995 | Leonardi et al. | 514/252 |
| 5,474,994 A | 12/1995 | Leonardi et al. | 514/218 |
| 5,569,659 A | 10/1996 | Reitz | 514/253 |
| 5,605,896 A | 2/1997 | Leonardi et al. | 514/218 |
| 5,859,014 A | 1/1999 | Bantle et al. | 514/255 |
| 6,046,329 A | 4/2000 | Püsse et al. | 544/295 |

FOREIGN PATENT DOCUMENTS

| | | |
|---|---|---|
| AU | A-38776/93 | 12/1993 |
| EP | 0 428 434 A2 | 5/1991 |
| EP | 0 428 434 A3 | 5/1991 |
| EP | 0 748 800 A3 | 12/1996 |
| EP | 0 748 800 A2 | 12/1996 |

OTHER PUBLICATIONS

Akiba–Kin–ya, et al., "Ring Transformation Equilibrium (Bond Switch) in the 5–(2–Aminovinyl)isothiazole System via Hypervalent Sulfurane, Synthesis, Structure Determination, and Kinetic Study", *J. Am. Chem. Soc.*, 107:2721–2730 (1985).

Albertson, Noel F, "Synthesis of Peptides with Mixed Anhydrides" in *Organic Reactions*, vol. 12, chapter 4:pp. 157–363 (1962).

Andersson, K.E et al., "Benign Prostatic Hyperplasia and α–Adrenoceptors in the Lower Urinary Tract"; *4th Intl. Consult. in BPH Paris*, Jul. 2–5, pp. 601–609 (1997).

Andersson, K.E, "Mode of Action of $\alpha_1$–Adrenoreceptor Antagonists in the Treatment of Lower Urinary Tract Symptoms", *BJU International*, 85:12–18 (2000).

Basha, Anwer, et al., "A Mild, General Method for Conversion of Esters to Amides", *Tetrahedron Letters*, 48:4171–4174 (1977).

Cheng, Yung–Chi, et al., "Relationship Between the Inhibition Constant ($K_I$) and the Concentration of Inhibitor Which Causes 50 Per Cent Inhibition ($I_{50}$) of an Enzymatic Reaction", *Biochemical Pharmacology*, 22:3099–3108 (1973).

Cotecchia, Susanna, et al., "Molecular Cloning and Expression of the cDNA for the Hamster $\alpha_1$–Adrenergic Receptor", *Proc. Natl. Acad. Sci. USA*, 85:7159–7163 (1988).

Cullen, Bryan R, "Use of Eukaryotic Expression Technology in the Functional Analysis of Cloned Genes", *Methods in Enzymology*, 152:684–704 (1987).

DeLean, A, et al.; "Simultaneous Analysis of Families of Sigmoidal Curves: Application to Bioassay, Radioligand Assay, and Physiological Dose–Response Curves"; *Am. J. Physiol*, 235:E97–E102 (1978).

Doherty, Annette, M, et al., "Design and Synthesis of Potent, Selective, and Orally Active Fluorine–Containing Renin Inhibitors"; *J. Med. Chem.*, 35:2–14 (1992).

Doyle, F.P, "Derivatives of 6–Aminopenicillanic Acid. Part VI.[1] Penicillins From 3–and 5–Phenylisoxazole–4–Carboxylic Acids and Their Alkyl and Halogen Derivatives", *J. Chem. Soc.*, 5838–5845 (1963).

Doyle, F.P, "Derivatives of 6–Aminopenicillanic Acid. Part VII.[1] Further 3,5–Disubstituted Isoxazole–4–Carboxylic Acid Derivatives", *J. Chem. Soc.*, 5845–5854 (1963).

Elworthy, T.R, et al., "N–Arylpiperazinyl–N'–propylamino Derivatives of Heteroaryl Amides as Functional Uroselective $\alpha_1$–Adrenoceptor Antagonists"; *J. Med. Chem.* 40:2674–2687 (1997).

Fargin, Annick, et al., "Effector Coupling Mechanism of the Cloned 5–HT1A Receptor"; *J. Biological Chemistry*; 284:14848–14852 (1989).

Fargin, Annick, et al., "The Genomic Clone G–21 Which Resembles a β–Adrenergic Receptor Sequence Encodes the 5–HT $_{1A}$ Receptor"; *Nature*; 335:358–360 (1988).

(List continued on next page.)

*Primary Examiner*—Richard L. Raymond
*Assistant Examiner*—Rao Uppu
(74) *Attorney, Agent, or Firm*—Darby & Darby

(57) ABSTRACT

The invention relates to novel N-(substituted phenyl)-N'-[ω-(3-substituted phenyl-4-isoxazolecarbonylamino)alkyl] piperazines, their N-oxides, and pharmaceutically acceptable salts thereof. The compounds are endowed with enhanced selectivity for alpha1-adrenergic receptors and a low activity in lowering blood pressure. The compounds are useful in the treatment of obstructive syndromes of the lower urinary tract, including benign prostatic hyperplasia (BPH), and in the treatment of lower urinary tract symptoms (LUTS) and neurogenic lower urinary tract dysfunction (NLUTD), and other conditions.

62 Claims, No Drawings

OTHER PUBLICATIONS

Fitzpatrick, J.M,"Facts and Future Lines of Research in Lower Urinary Tract Symptoms in Men and Women: An Overview of the Role of $\alpha_1$–Adrenoreceptor Antagonists", *BJU International*, 85(Suppl. 2):1–5 (2000).

Flavahan, N.A, et al., "$\alpha_1$–Adrenoceptor Subclassification in Vascular Smooth Muscle", *Trends Pharmacol Sci*, 7:347–349 (1986).

Ford, Anthony, P.D.W, et al., "Do$\alpha_{1A}$ ($\alpha_{1C}$)–Adrenoceptors (AR) Mediate Prostatic Smooth Muscle Contraction in Man? Studies with a Novel, Selective $\alpha_{1A}$–AR Antagonist, RS 17053", *Br. J. Pharmacol*, 114:24 P (1995).

Furchgott, R.E, "The Classification of Adrenoceptors (Adrenergic Receptors). An Evaluation From the Standpoint of Receptor Theory", in *Handbook of Experim. Pharmacology—New Series*, Chapter 9, pp. 283–335 (1972).

Gibson, M.S, "The Introduction of the Amino Group", in *The Chemistry of the Amino Group*, S. Patai (Ed.), John Wiley & Sons, N.Y. , chapter 2, pp. 37–66 (1968).

Gozlan, H, et al., "Photoaffinity Labelling and Solubilization of the Central 5–HT$_{1A}$ Receptor Binding Site", *J. Receptor Res.*, 7:195–221 (1987).

Hamper, Bruce C, et al., "Syn thesis and Herbicidal Activity of Aryl-5-(haloalkyl)-4-Isoxazolecarbixamides and Their Derivatives" *J. Agric. Food Chem*, 43:219–228 (1995).

Hendrickson, James. B, et al., "Triflamides: New Acylating and Triflating Reagents", *Tetrahedron Letters*, 46:4607–4610 (1973).

Hieble, Paul, J, et al., "International Union of Pharmacology X. Recommendation for Nomenclature of $\alpha_1$–Adrenoceptors: Consensus Update", *Pharmacological Reviews* 47:267–270 (1995).

Imagawa, Jun–Ichi, et al., "Functional Evaluation of Sympathetically Mediated Responses in In Vivo Lower Urinary Tract of Dogs", *J. Pharmacol Methods*, 22:103–111 (1989).

Ishihara, Yuji, et al., "Central Cholinergic Agents. II. [1] Synthesis and Acetylcholinesterase Inhibitory Activities of N–[ω–[N–Alkyl–N–(phenylmethyl) amino]alkyl]–3–aryl-propenamides", *Chem. Pharm. Bull*, 39:3236–3243 (1991).

Kakizaki, H, et al., "Current View and Status of the Treatment of Lower Urinary Tract Symptoms and Neurogenic Lower Urinary Tract Dysfunction", *BJU International*, 85(Suppl.2):25–30 (2000).

Kenny, B.A, et al., "Evaluation of the Pharmacological Selectivity Profile of $\alpha_1$ Adrenoceptor Antagonists at Prostatic $\alpha_1$ Adrenoceptors: Binding, Functional and In Vivo Studies", *Br. J. Pharmacol*, 118:871–878 (1996).

Kobilka, Brian K, et al., "An Intronless Gene Encoding a Potential Member of the Family of Receptors Coupled To Guanine Nucleotide Regulatory Proteins", *Nature* , 329:75–79 (1987).

Leonardi, A, et al., "Pharmacological Characterization of the Uroselective Alpha–1 Antagonist Rec 15/2739 (SB 216469): Role of the Alpha–1L Adrenoceptor in Tissue Selectivity, Part 1", *J. Pharmacol. Exp. Ther.* 281:1272–1283 (1997).

Lipton, Michael, F, et al., "Conversion of Esters to Amides With Dimethylaluminum Amides: N,N–Dimethylcyclohexanecarboxamide", *Organic Syntheses.*, 59:49–53 (1979).

Malloy, Brian, et al., "$\alpha_1$–Adrenergic Receptor Subtypes in Human Detrusor", *J. Urology*, 160:937–943 (1998).

McGrath, J.C, et al., "Alpha–Adrenoceptors: A Critical Review", *Medicinal Research Reviews*, 9:407–533 (1989).

McGuire, Edward J, et al., "Effect of Alpha–Adrenergic Blockade and Anticholinergic Agents on the Decentralized Primate Bladder", *Neurourology and Urodynamics*, 4:139–142 (1985).

McKenna, John I, et al., "Cardioactivity and Solid–State Structure of Two 4–Isoxazolyldihydropyridines Related to the 4–Aryldihydropyridine Calcium–Channel Blockers", *J. Med. Chem.*, 31:473–476 (1988).

Michel, Martin, C, et al., "Radioligand Binding Studies of $\alpha_1$–Adrenoceptor Subtypes in Rat Heart", *Brit. J. Pharmacol*, 111:533–538 (1994).

Mitchell, James A, et al., "The Preparation of Aliphatic Amides", *J. Am. Chem. Soc.*, 53:1879–1883(1931).

Muramatsu, Ikunobu, et al., "Functional Subclassification of Vascular $\alpha_1$–Adrenoceptors", *Pharmacology Communications*, 6:23–28 (1995).

Natale, N.R, et al., "4–Isoxazolyl–1,4–dihydropyridines: Biological, Theoretical, and Structural Studies", *J. Med. Chem.*, 33:2255–2259 (1990).

Natale, N.R, et al., "Metalation of Isoxazolyloxazolines, a Facile Route to Functionally Complex Isoxazoles: Utility, Scope, and Comparison to Dianion Methodolgy", *J. Org. Chem.*, 50:5660–5666 (1985).

Oshita, Masafumi, et al., "Pharmacological Characterization of Two Distinct $\alpha_1$–Adrenoceptor Subtypes in Rabbit Thoracic Aorta", *Br. J. Pharmacol.*, 108:1071–1076 (1993).

Prelog, V, et al., *Collect. Czech. Chem. Comm.*, 5:497–502 (1933).

Schwinn, Debra, A, et al., "Molecular Cloning and Expression of the cDNA for a Novel $\alpha_1$–Adrenergic Receptor Subtype", *J. Biol. Chem.*, 265:8183–8189 (1990).

Serels, Scott, et al., "Prospective Study Comparing Hyoscyamine, Doxazosin, and Combination Therapy for the Treatment of Urgency and Frequency in Women", *Neurourology and Urodynamics*, 17:31–36 (1998).

Sundin Torsten, et al., "The Sympathetic Innervation and Adrenoreceptor Function of the Human Lower Urinary Tract in the Normal State and After Parasympathetic Denervation", *Investigative Urology*. 14:322–328 (1977).

Swierzewski, Stanley J, et al., "The Effect of Terazosin on Bladder Function in the Spinal Cord Injured Patient" *J. Urology.*, 151:951–954 (1994).

Testa, R, et al., "Pharmacological Characterization of the Uroselective Alpha–1 Antagonist Rec 15/2739 (SB 216469): Role of the Alpha–1L Adrenoceptor in Tissue Selectivity, Part II", *J. Pharmacology and Experimental Therapeutics*, 281:1284–1293 (1997).

Testa, R, et al., "Rec 15/2739 (SB 216469): A Novel Prostate Selective $\alpha_1$–Adrenoceptor Antagonist", *Pharmacology Communications*, 6:79–86 (1995).

* cited by examiner

ISOXAZOLECARBOXAMIDE DERIVATIVES

This patent application is based on Provisional Patent Application Ser. No. 60/218,314, filed on Jul. 14, 2000, which is hereby incorporated by reference. Applicants claim the benefit of the filing date of the aforesaid Provisional Application under 35 U.S.C. §119(e)(1).

Applicants also claim priority under 35 U.S.C. §119(a–d) of Italian patent application no. MI99A 002173, filed Oct. 18, 1999, which is hereby incorporated by reference.

SCOPE OF THE INVENTION

The present invention relates to isoxazolecarboxamide derivatives, to pharmaceutical compositions containing them and to uses for such derivatives and compositions.

BACKGROUND OF THE INVENTION

U.S. Pat. No. 5,403,842, Leonardi et al., and its continuations (U.S. Pat. No. 5,474,994, Leonardi et al. and U.S. Pat. No. 5,605,896, Leonardi et al.) claim heterobicyclic derivatives bearing substituted phenylpiperazines linked to the heterocyclic ring by a variety of spacer groups. Among said derivatives, compound A (Ex. 11) is of particular interest due its high activity and uroselectivity.

Compound A

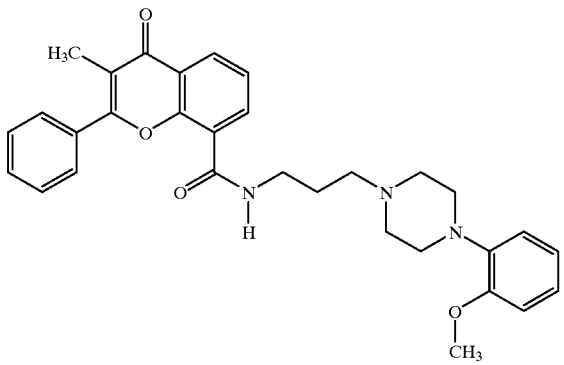

Compound A is endowed with good affinity for the $\alpha_{1A}$ adrenoceptor and is able to selectively inhibit contractility of the prostatic urethra in a dog model without substantial effects on blood pressure (Leonardi et al., J. Pharmacol. Exp. Therap., 281:1272–1283, 1997).

N,ω-Aminoalkylamides of 3-phenyl-4-isoxazolecarboxylic acid are known compounds, but prior-art molecules possess quite diverse molecular structures as compared to those claimed in this patent and a completely different pharmacological effect. For example, European patent EP 0573883, Jeschke et al., includes, as a representative compound, 3-(2-chloro-6-fluorophenyl)-N-[3-(2-chlorophenylamino)propyl]-5-methyl-isoxazole-4-carboxamide and other similar derivatives and their claimed therapeutic application is the care of endoparasitoses. European patent EP 0428434, Emonds-Alt et al., claims 3-(2-chlorophenyl)-N-{2-(3,4-dichlorophenyl)-4-[4-(phenylmethyl)-1-piperidinyl]butyl}-5-methylisoxazole-4-carboxamide as substance P antagonists. Neither of these patents claim arylpiperazinyl derivatives active at the $\alpha_1$ adrenergic receptor.

The present invention is directed to the structural class of N-(substituted phenyl)-N'-[ω-(3-substituted phenyl-4-isoxazolecarbonylamino)alkyl]piperazines. The compounds of this class are endowed with enhanced selectivity toward the $\alpha_1$ adrenergic receptor (with or without further selectivity for the $\alpha_{1A}$ receptor or for both the $\alpha_{1A}$ and $\alpha_{1D}$), in particular with respect to the 5-HT$_{1A}$ receptor, and improved in vivo uroselectivity even compared to compound A, with remarkable effects on relaxation of prostatic urethra and very low activity in lowering blood pressure. This activity profile suggests the safer use of the compounds of the invention in the therapy of obstructive syndromes of the lower urinary tract, including benign prostatic hyperplasia (BPH); of lower urinary tract symptoms (LUTS); and neurogenic lower urinary tract dysfunction (NLUTD), without side-effects associated with hypotensive activity.

SUMMARY OF THE INVENTION

The invention provides compounds of the general formula I:

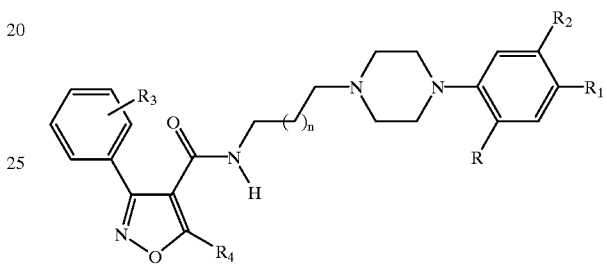

wherein:

R is selected from the group consisting of alkyl, alkoxy, polyfluoroalkoxy, hydroxy and trifluoromethanesulfonyloxy group;

each of $R_1$ and $R_2$ independently is selected from the group consisting of a hydrogen, halogen, polyfluoroalkoxy and alkoxy group;

$R_3$ represents one or more substituents selected from the group consisting of hydrogen, halogen, alkyl, alkoxy, nitro, amino, acylamino, cyano, alkoxycarbonyl, carboxamido group;

$R_4$ is selected from the group consisting of a hydrogen atom, an alkyl group and an arylalkyl group; and n is 0, 1 or 2.

The invention also includes the N-oxides and pharmaceutically acceptable salts of these compounds.

Preferred alkyl groups which R and $R_4$ may represent are without limitation lower ($C_{1-4}$) alkyl groups, most preferably methyl ($CH_3$). Preferred alkoxy groups which R, $R_1$, $R_2$ and $R_3$ may represent without limitation are lower ($C_{1-4}$) alkoxy groups, most preferably methoxy. Preferred polyfluoroalkoxy groups which R, $R_1$ and $R_2$ may represent are without limitation trifluoromethoxy or 2,2,2-trifluoroethoxy groups. The preferred value for n is 1.

A preferred arylalkyl group that $R_4$ may represent without limitation is phenyl, optionally substituted with one or more substituent selected from the group consisting of hydrogen, halogen, $C_{1-4}$ alkyl, alkoxy, nitro, amino, acylamino, cyano, alkoxycarbonyl and carboxamido group.

A preferred group that $R_3$ may represent without limitation is carboxamido.

Also preferred is where R is selected from the group consisting of alkoxy and hydroxy; $R_1$ is selected from the group consisting of hydrogen and halogen; $R_2$ is selected from the group consisting of hydrogen and halogen; $R_3$ represents one or more substitutents consisting of hydrogen, halogen, alkyl, alkoxy, nitro, amino, acylamino, cyano, alkoxycarbonyl and carboxamido group; $R_4$ is selected from the group consisting of hydrogen and alkyl; and n is 0, 1 or 2.

Also preferred is where R is selected from a group consisting of alkoxy, alkyl and polyfluoroalkoxy; $R_1$ is selected from the group consisting of hydrogen, halogen and alkoxy; $R_2$ is selected from the group consisting of hydrogen, halogen and alkoxy; $R_3$ represents one or more substitutents selected from the group consisting of hydrogen, halogen, alkyl, alkoxy, and amino; $R_4$ is selected from the group consisting of hydrogen and alkyl; and n is 0, 1 or 2.

Also preferred is where R is selected from the group consisting of alkoxy, alkyl and polyfluoroalkoxy; $R_1$ is halogen; $R_2$ is hydrogen; $R_3$ represents one or more substitutents selected from the group consisting of hydrogen, halogen, alkyl, alkoxy and amino; $R_4$ is selected from the group consisting of hydrogen and alkyl; and n is 0, 1 or 2.

The compounds of the invention include those compounds where, independently, R is selected from the group consisting of methyl, methoxy, 2,2,2,-trifluoroethoxy, hydroxy and trifluoromethanesulfonyloxy, $R_1$ is selected from a group consisting of hydrogen and fluorine, $R_2$ is selected from the group consisting of a hydrogen, chlorine and 2,2,2-trifluoroethoxy, $R_3$ is carboxamido, $R_4$ is selected from the group consisting of methyl, ethyl, 2-phenylethyl, 3-phenylpropyl and hydrogen; and n is 0, 1 or 2.

Other compounds within the invention are those compounds with combinations of substituents where, together, R is selected from the group consisting of methyl, methoxy, 2,2,2,-trifluoroethoxy, hydroxy and trifluoromethanesulfonyloxy and $R_1$ is selected from the group consisting of hydrogen and fluorine; or R is selected from the group consisting of methyl, methoxy, 2,2,2,-trifluoroethoxy, hydroxy and trifluoromethanesulfonyloxy and $R_2$ is selected from the group consisting of a hydrogen, chlorine and 2,2,2-trifluoroethoxy; or R is selected from the group consisting of methyl, methoxy, 2,2,2,-trifluoroethoxy, hydroxy and trifluoromethanesulfonyloxy and $R_3$ is carboxamido; or R is selected from the group consisting of methyl, methoxy, 2,2,2,-trifluoroethoxy, hydroxy and trifluoromethanesulfonyloxy and $R_4$ is selected from the group consisting of methyl, ethyl, 2-phenylethyl, 3-phenylpropyl and hydrogen. For each of these combinations, n is 0, 1, or 2.

Compounds of the invention also include those compounds with combinations of substituents where, together, $R_1$ is selected from the group consisting of hydrogen and fluorine and $R_2$ is selected from the group consisting of a hydrogen, chlorine and 2,2,2-trifluoroethoxy; or $R_1$ is selected from the group consisting of hydrogen and fluorine and $R_3$ is carboxamido; or $R_1$ is selected from the group consisting of hydrogen and fluorine and $R_4$ is selected from the group consisting of methyl, ethyl, 2-phenylethyl, 3-phenylpropyl and hydrogen. For each of these combinations, n is 0, 1, or 2.

Also included within the invention are compounds with combinations of substituents where, together, $R_2$ is selected from the group consisting of a hydrogen, chlorine and 2,2,2-trifluoroethoxy and $R_3$ is carboxamido; or $R_2$ is selected from the group consisting of a hydrogen, chlorine and 2,2,2-trifluoroethoxy and $R_4$ is selected from the group consisting of methyl, ethyl, 2-phenylethyl, 3-phenylpropyl and hydrogen; or $R_3$ is carboxamido and $R_4$ is selected from the group consisting of methyl, ethyl, 2-phenylethyl, 3-phenylpropyl and hydrogen. For each of these combinations, n is 0, 1, or 2.

The invention also includes compounds having combinations of substituents where, together, R is selected from the group consisting of methyl, methoxy, 2,2,2,-trifluoroethoxy, hydroxy and trifluoromethanesulfonyloxy, $R_1$ is selected from the group consisting of hydrogen and fluorine and $R_2$ is selected from the group consisting of a hydrogen, chlorine and 2,2,2-trifluoroethoxy; or R is selected from the group consisting of methyl, methoxy, 2,2,2,-trifluoroethoxy, hydroxy and trifluoromethanesulfonyloxy, $R_1$ is selected from the group consisting of hydrogen and fluorine and $R_3$ is carboxamido; or R is selected from the group consisting of methyl, methoxy, 2,2,2,-trifluoroethoxy, hydroxy and trifluoromethanesulfonyloxy, $R_1$ is selected from the group consisting of hydrogen and fluorine and $R_4$ is selected from the group consisting of methyl, ethyl, 2-phenylethyl, 3-phenylpropyl and hydrogen; or R is selected from the group consisting of methyl, methoxy, 2,2,2,-trifluoroethoxy, hydroxy and trifluoromethanesulfonyloxy, $R_2$ is selected from the group consisting of a hydrogen, chlorine and 2,2,2-trifluoroethoxy and $R_3$ is carboxamido; or R is selected from the group consisting of methyl, methoxy, 2,2,2,-trifluoroethoxy, hydroxy and trifluoromethanesulfonyloxy, $R_2$ is selected from the group consisting of a hydrogen, chlorine and 2,2,2-trifluoroethoxy and $R_4$ is selected from the group consisting of methyl, ethyl, 2-phenylethyl, 3-phenylpropyl and hydrogen; or R is selected from the group consisting of methyl, methoxy, 2,2,2,-trifluoroethoxy, hydroxy and trifluoromethanesulfonyloxy, $R_3$ is carboxamido and $R_4$ is selected from the group consisting of methyl, ethyl, 2-phenylethyl, 3-phenylpropyl and hydrogen. For each of these combinations, n is 0, 1, or 2.

The compounds of the invention also include compounds having combinations of substituents where, together, $R_1$ is selected from the group consisting of hydrogen and fluorine, $R_2$ is selected from the group consisting of a hydrogen, chlorine and 2,2,2-trifluoroethoxy and $R_3$ is carboxamido; or $R_1$ is selected from the group consisting of hydrogen and fluorine, $R_2$ is selected from the group consisting of a hydrogen, chlorine and 2,2,2-trifluoroethoxy and $R_4$ is selected from the group consisting of methyl, ethyl, 2-phenylethyl, 3-phenylpropyl and hydrogen; or $R_1$ is selected from the group consisting of hydrogen and fluorine, $R_3$ is carboxamido and $R_4$ is selected from the group consisting of methyl, ethyl, 2-phenylethyl, 3-phenylpropyl and hydrogen; or $R_2$ is selected from the group consisting of a hydrogen, chlorine and 2,2,2-trifluoroethoxy, $R_3$ is carboxamido and $R_4$ is selected from the group consisting of methyl, ethyl, 2-phenylethyl, 3-phenylpropyl and hydrogen. For each of these combinations, n is 0, 1, or 2.

Other compounds within the invention are those with combinations of substituents where, together, $R_1$ is selected from the group consisting of hydrogen and fluorine, $R_2$ is selected from the group consisting of a hydrogen, chlorine and 2,2,2-trifluoroethoxy, $R_3$ is carboxamido and $R_4$ is selected from the group consisting of methyl, ethyl, 2-phenylethyl, 3-phenylpropyl and hydrogen; or R is selected from the group consisting of methyl, methoxy, 2,2,2,-trifluoroethoxy, hydroxy and trifluoromethanesulfonyloxy, $R_2$ is selected from the group consisting of a hydrogen, chlorine and 2,2,2-trifluoroethoxy, $R_3$ is carboxamido, and $R_4$ is selected from the group consisting of methyl, ethyl, 2-phenylethyl, 3-phenylpropyl and hydrogen; or R is selected from the group consisting of methyl, methoxy, 2,2,2,-trifluoroethoxy, hydroxy and trifluoromethanesulfonyloxy, $R_1$ is selected from the group consisting of hydrogen and fluorine, $R_3$ is carboxamido and $R_4$ is selected from the group consisting of methyl, ethyl, 2-phenylethyl, 3-phenylpropyl and hydrogen; or R is selected from the group consisting of methyl, methoxy, 2,2,2,-trifluoroethoxy, hydroxy and trifluoromethanesulfonyloxy, $R_1$ is selected from the group consisting of hydrogen and fluorine, $R_2$ is selected from the group consisting of a hydrogen, chlorine and 2,2,2-trifluoroethoxy and $R_4$ is selected from the group consisting of methyl, ethyl, 2-phenylethyl, 3-phenylpropyl and hydrogen; or R is selected from the group consisting of methyl, methoxy, 2,2,2,-trifluoroethoxy, hydroxy and trifluoromethanesulfonyloxy, $R_1$ is selected from the group consisting of hydrogen and fluorine, $R_2$ is selected from the group consisting of hydrogen, chlorine and 2,2,2-trifluoroethoxy and $R_3$ is carboxamido. For each of these combinations, n is 0, 1, or 2.

Still other compounds within the invention are those compounds where together R is selected from the group consisting of methyl, methoxy, 2,2,2,-trifluoroethoxy, hydroxy and trifluoromethanesulfonyloxy, $R_1$ is selected from a group consisting of hydrogen and fluorine, $R_2$ is selected from the group consisting of a hydrogen, chlorine and 2,2,2-trifluoroethoxy, $R_3$ is carboxamido, $R_4$ is selected from the group consisting of methyl, ethyl, 2-phenylethyl, 3-phenylpropyl and hydrogen; and n is 0, 1 or 2.

The invention further provides pharmaceutical compositions comprising a compound of the general formula I or an N-oxide or pharmaceutically acceptable salt of such a compound, in admixture with a pharmaceutically acceptable diluent or carrier. Preferences are as outlined above for the compounds of the invention.

In another aspect, the invention is directed to methods for selectively preventing contractions (including noradrenaline-mediated contractions) of the urethra and lower urinary tract, without substantially affecting blood pressure, by administering one or more selected compounds of the general formula I to a mammal (including a human) in need of such treatment in an amount or amounts effective for the particular use.

In yet another aspect, the invention is directed to methods for blocking $\alpha_1$ receptors by exposing said receptors (e.g, by delivery to the environment of said receptors, by addition to an extracellular medium, or by administering to a mammal possessing said receptors) an effective amount of a compound of the invention, in this way relieving diseases associated to overactivity of said receptors.

It is a primary object of the present invention to provide a method of treating BPH which avoids any undue side effects due to acute hypotension (i.e., limited effects on blood pressure).

It is another object of the present invention to provide pharmaceutical compositions comprising isoxazole compounds which are selective $\alpha_1$ adrenoceptor antagonists, which compositions are effective for the treatment of BPH optionally including a carrier or diluent.

It is another object of the present invention to provide a method of treating BPH using isoxazole compounds which are selective $\alpha_1$ adrenoceptor antagonists.

Another aspect of the invention is the use of new compounds for lowering intraocular pressure, inhibiting cholesterol synthesis, reducing sympathetically-mediated pain and the treatment of cardiac arrhythmia and erectile dysfunction, as well as LUTS and NLUTD.

An object of the present invention is to provide a method of preventing contractions of the urethra and lower urinary tract comprising administering to a mammal including a human in need of such treatment an effective amount of compounds of the present invention and/or pharmaceutical compositions comprising compounds of the present invention.

A further object of the present invention is a method of administration of compounds of the present invention or pharmaceutical compositions comprising compounds of the present invention to mammals including humans which causes very limited effects on the blood pressure of said mammal.

As used herein, "limited effect on blood pressure" and "without substantial effect on blood pressure" are defined as effects on blood pressure that are without clinical significance. In experimental animals, "limited" and "without substantial" effects on blood pressure are defined as lowering blood pressure by about 10% or less, compared to control animals. In humans, "limited" and "without substantial" effects on blood pressure are defined as effects wherein diastolic blood pressure is reduced by less than about 5 mm Hg.

A further object of the present invention is a method for blocking $\alpha_1$ adrenergic receptors comprising releasing in the environment of said receptors compounds of the present inventions or pharmaceutical compositions of the present invention to relieve diseases associated with overactivity of said receptor.

A further object of the present invention is the release of compounds of the present invention or pharmaceutical compositions containing compounds of the present invention in the environment of $\alpha_1$ adrenergic receptors wherein said release is effected by administering compounds of the present invention or pharmaceutical compositions containing compounds of the present invention to a mammal including a human possessing said receptors.

A further object of the present invention is the method of treatment of a patient suffering from benign prostatic hyperplasia, the method comprising administering an effective amount of a compound of the present invention or a pharmaceutical composition containing a compound of the present invention to a patient in need of such treatment.

A further object of the present invention is the method of treatment of a patient suffering from excessive intraocular pressure, the method comprising administering an effective amount of a compound of the present invention or a pharmaceutical composition containing a compound of the present invention to a patient in need of such treatment.

A further object of the present invention is the method of treatment of a patient suffering from cardiac arrhythmia, the method comprising administering an effective amount of a compound of the present invention or a pharmaceutical composition containing a compound of the present invention to a patient in need of such treatment.

A further object of the present invention is the method of treatment of a patient suffering from erectile dysfunction, the method comprising administering an effective amount of a compound of the present invention or a pharmaceutical composition containing a compound of the present invention to a patient in need of such treatment.

A further object of the present invention is the method of treatment of a patient suffering from sexual dysfunction, the method comprising administering an effective amount of a compound of the present invention or a pharmaceutical composition containing a compound of the present invention to a patient in need of such treatment.

A further object of the present invention is the method for inhibiting cholesterol biosynthesis, the method comprising administering an effective amount of a compound of the present invention or a pharmaceutical composition containing a compound of the present invention to a patient in need of such treatment.

A further object of the present invention is the method for reducing sympathetically mediated pain, the method comprising administering an effective amount of a compound of the present invention or a pharmaceutical composition containing a compound of the present invention to a patient in need of such treatment.

It is understood that "sympathetically-mediated" is defined as any physiological sensation, condition or response that depends upon any component of the sympathetic nervous system, can be modulated by the action of any component of the sympathetic nervous system, or can be affected by treatment of any component of the sympathetic nervous system.

A further object of the present invention is the method for the treatment of lower urinary tract symptoms (LUTS), which include but are not limited to filling symptoms, urgency, incontinence and nocturia, as well as voiding problems such as weak stream, hesitance, intermittency, incomplete bladder emptying and abdominal straining, the method comprising administering an effective amount of a compound of the present invention or a pharmaceutical composition containing a compound of the present invention to a patient in need of such treatment, optionally farther comprising the inclusion of an anticholinergic compound which may be selected from the group consisting of tolterodine, oxybutinin, darifenacin, alvameline and temiverine.

A further object of the present invention is the method for the treatment of neurogenic lower urinary tract dysfunction (NLUTD), the method comprising administering an effective amount of a compound of the present invention or a pharmaceutical composition containing a compound of the present invention to the patient, optionally further comprising the inclusion of an anticholinergic compound which may be selected from the group consisting of tolterodine, oxybutinin, darifenacin, alvameline and temiverine.

A further object of the present invention is the treatment of LUTS in females which include but are not limited to filling symptoms, urgency, incontinence, and nocturia as well as voiding problems such as weak stream, hesitance, intermittency, incomplete bladder emptying, and abdominal straining, the method comprising administering an effective amount of a compound of the present invention or a pharmaceutical composition containing a compound of the present invention to a woman in need of such treatment, optionally further comprising the inclusion of an anticholinergic compound which may be selected from the group consisting of tolterodine, oxybutinin, darifenacin, alvameline and temiverine.

For all uses and methods described herein, preferences are as outlined above for the compounds of the invention.

Other features and advantages of the present invention will be apparent to those skilled in the art from the following detailed description and claims.

DETAILED DESCRIPTION OF THE INVENTION

All patents, patent applications, and literature references cited in this application are incorporated by reference in their entirety.

The adrenergic antagonistic activity of the compounds of the invention renders them useful as agents acting on body tissues particularly rich in $\alpha_1$ adrenergic receptors (such as prostate and urethra). Accordingly, anti-adrenergic compounds within the invention, established as such on the basis of their receptor binding profile, can be useful therapeutic agents for the treatment, for example, of micturition problems associated with obstructive disorders of the lower urinary tract, including but not limited to benign prostatic hyperplasia (BPH).

BPH is a progressive condition, which is characterized by a nodular enlargement of prostatic tissue resulting in obstruction of the urethra. This results in increased frequency of urination, nocturia, a poor urinary stream and hesitancy or delay in starting urine flow. Chronic consequences of BPH can include hypertrophy of bladder smooth muscle, a decompensated bladder and an increased incidence of urinary tract infection. The specific biochemical, histological and pharmacological properties of the prostate adenoma leading to bladder outlet obstruction are not yet known. However, the development of BPH is considered to be an inescapable phenomenon for the ageing male population. BPH is observed in approximately 70% of males over the age of 70. Currently, the worldwide stated method of choice for treating. BPH is surgery. A medicinal alternative to surgery is clearly very desirable. The limitations of surgery for treating BPH include the morbidity rate of an operative procedure in elderly men, persistence or recurrence of obstructive and irritative symptoms, as well as the significant cost of surgery.

$\alpha$-Adrenergic receptors (McGrath et. al., Med. Res. Rev., 9:407–533, 1989) are specific neuroreceptor proteins located in the peripheral and central nervous systems on tissues and organs throughout the body. These receptors are important targets for controlling many physiological functions and thus represent important targets for drug development. In fact, many $\alpha$-adrenergic drugs have been developed over the past 40 years. Examples include clonidine, phenoxybenzamine and prazosin, terazosin, alfuzosin, doxazosin, tamsulosin (treatment of hypertension), naphazoline (nasal decongestant), and apraclonidine (treating glaucoma). $\alpha$-Adrenergic drugs can be broken down into two distinct classes: agonists (clonidine and naphazoline are agonists), which mimic the receptor activation properties of the endogenous neurotransmitter noradrenaline, and antagonists (phenoxybenzamine and prazosin, terazosin, alfuzosin, doxazosin and tamsulosin are antagonists), which act to block the effects of noreadrenaline. Many of these drugs are effective but also produce unwanted side effects (for example, clonidine produces dry mouth and sedation in addition to its antihypertensive effects).

The above reported agonists are selective for the $\alpha_2$ adrenergic receptor whereas most antagonists are selective for the $\alpha_1$ adrenoceptor, with the exception of tamsulosin which shows a comparable affinity also for the 5-HT$_{1A}$ receptor. Many of the cited $\alpha_1$ antagonists are currently used for the therapy of BPH but, due to their poor uroselectivity, they are liable to cause cardiovascular side effects.

Recent pharmacological, biochemical and radioligand-binding studies evidenced three different $\alpha_1$-receptor subtypes with a high affinity for prazosin, namely $\alpha_{1A-}$ ($\alpha_{1a-}$), $\alpha_{1B-}$ ($\alpha_{1b-}$) and $\alpha_{1D-}$ ($\alpha_{1d-}$), with lower case subscripts being used for recombinant receptors and upper case subscripts for receptors in native tissues (Hieble et al., Pharmacol. Rev., 47:267–270, 1995). In functional studies $\alpha_1$ receptors with a low affinity for prazosin have also been identified and termed $\alpha_{1L}$ receptors (Flavahan et al., Trends Pharmacol. Sci., 7:347–349, 1986; Muramatsu et al., Pharmacol. Comm., 6:23–28, 1995).

Several studies have demonstrated the presence of these $\alpha_1$-adrenergic-receptor subtypes in the lower-urinary-tract tissues (Andersson K. E., 4th International Consultation in Benign Prostatic Hyperplasia (BPH)", Paris, Jul. 2–5, 1997, pages 601–609).

Several studies have shown that the human prostate receives innervation from both the sympathetic and parasympathetic nervous systems.

The adrenergic nerves are considered responsible for prostatic smooth-muscle tone by releasing noradrenaline, stimulating contraction-mediating $\alpha_1$-adrenergic receptors. Approximately 50% of the total urethral pressure in BPH patients may be due to $\alpha_1$-adrenoceptor-mediated muscle tone. Functional studies have indicated the occurrence of important adrenoceptor functions in prostatic adenomatous and capsular tissue. Clinical studies with the prototypical $\alpha_1$-adrenoceptor-selective antagonist, prazosin, enforced the key role of $\alpha_1$ adrenoceptors in the control of prostatic smooth-muscle tone. This was also confirmed in the laboratory by studies showing that, although both $\alpha_1$ and $\alpha_2$ adrenoceptors can be identified within the human prostate, contractile properties are mediated primarily by $\alpha_1$ adrenoceptors. Many clinical investigations have confirmed that $\alpha_1$-adrenoceptor blockade relieves lower-urinary-tract symptoms (LUTS), both of irritative and obstructive type, in patients with BPH.

Lower urinary tract symptoms (LUTS) also develop in women as they age. As in men, LUTS in women includes both filling symptoms such as urgency, incontinence, and nocturia, and voiding symptoms, such as weak stream, hesitancy, intermittency, incomplete bladder emptying and abdominal straining. That both men and women experience a similar high prevalence of filling and voiding LUTS suggests that at least part of the underlying etiology may be identical. In a recent study, an $\alpha_1$-antagonist was reported to reduce LUTS in women to a greater extent than an anticholinergic (Serels, S. and Stein, M., Neurology and Urodynamics 17: 31–36, 1998). The authors concluded that there appeared to be a role for $\alpha_1$-antagonists in treating LUTS in women. The possible mechanisms implicated to explain these results are: a) dysfunction of the bladder neck and urethra, causing functional outlet obstruction, analogous to BPH-induced outlet obstruction, with secondary detrusor overactivity; and b) increased $\alpha_1$-adrenoceptor activity in the detrusor, causing frequency and urgency. On these bases, $\alpha_1$-antagonists are used in clinical practice to treat LUTS in women (Fitzpatrick, International British J. Urol. 85, Supp. 2: 1–5, 2000; Kakizaki, M. et al., Brit. J. Urol. International 85, Supp. 2: 25–30, 2000). The results of Serels also indicate that the combined administration of $\alpha_1$-antagonists and anticholinergics can have improved efficacy in treatment of LUTS, as suggested by Fitzpatrick (International British J. Urol. 85, Supp. 2: 1–5, 2000).

Another possible use of $\alpha_1$-antagonists is the management of neurogenic lower urinary tract dysfunction (NLUTD), as can be caused by neurological disease or trauma. NLUTD may lead to debilitating symptoms and serious complications, including increased urinary frequency, incontinence, voiding difficulty, recurrent upper urinary tract infections, and upper urinary tract deterioration. Management of NLUTD is indicated to preserve renal function and avoid urological complications. Administration of $\alpha_1$-antagonists may benefit patients with NLUTD by facilitating urine storage by alleviating high detrusor pressure during bladder filling, which is evidenced by poor bladder compliance and detrusor hyperreflexia. In both animal models and patients with spinal cord injury resistant to anticholinergics, $\alpha_1$-antagonists improved bladder compliance. (Kakizaki, M. et al., Brit. J. Urol International 85, Supp.2: 25–30, 2000); Sundin, T. et al., Invest Urol. 14: 322–328, 1977; McGuire et al., Neurology and Urodynamics 4: 139–142, 1985; Swierzewski, S. J. etal., J. Urol. 151: 951–954, 1994).

Two distinct $\alpha_1$-adrenoceptor subtypes have been suggested to be present in the human prostate, one ($\alpha_{1H}$) with high and one ($\alpha_{1L}$) with low affinity for prazosin. All three high-affinity $\alpha_1$-adrenoceptor subtypes found in molecular cloning studies have been identified in prostatic stromal tissue. The $\alpha_{1a}$ subtype was found to be the dominant, representing about 60–85% of the $\alpha_1$-adrenoceptor population. Recent findings suggest that there may be differences in subtype populations between normal and hyperplastic prostates, the ratios between the subtypes $\alpha_{1a}:\alpha_{1b}:\alpha_{1d}$ being 85:1:14 in BPH tissue and 63:6:31 in non-BPH tissue.

The $\alpha_{1A}$ adrenoceptor was reported to mediate the contractile response of the human prostate in vitro. Ford et al. (Br. J. Pharmacol., 114:24 P, 1995) found that the $\alpha_{1A}$ adrenoceptor may not mediate contractile responses to noradrenaline, and suggested as a candidate the $\alpha_{1L}$ adrenoceptor. Findings by Kenny et al. (Br. J. Pharmacol., 118:871–878, 1996) support the view that the $\alpha_{1L}$ adrenoceptor, which appears to share many of the characteristics of an $\alpha_{1A}$ adrenoceptor, mediates the contractile response of the human prostate.

In the female urethra, mRNA for the $\alpha_1$ subtype was predominant and autoradiography confirmed the predominance of the $\alpha_{1A}$ adrenoceptor (Andersson, K. E., Brit. J. Urol. Intl. 85, Supp. 2: 12–18, 2000). The $\alpha_{1A}$ and $\alpha_{1D}$ subtypes are reported to be present in the human detrusor, with the latter subtype predominant (Malloy B. et al., J. Urol. 160: 937–943, 1998). Accordingly, the evidence that $\alpha_1$ adrenoreceptor antagonists are useful in treating lower urinary tract symptoms of both prostatic and non-prostatic origin in both males and females can be used to support the usefulness of the compounds of the present invention in treating such symptoms regardless of whether they are of obstructive origin or not and regardless of the sex of the patient.

On the other hand, it has also been suggested that the $\alpha_{1A}$ and $\alpha_{1L}$ adrenoceptors may represent distinct pharmacological forms of the same receptor.

The affinity of the compounds of the invention for each receptor can be assessed by receptor binding assays, for example as follows:

(1) $\alpha_1$-adrenergic-receptor subtypes: using the specific ligand $^3$H-prazosin, according to Testa R. et al., Pharmacol. Comm. 6: 79–86, 1995; Cotecchia S. et al., Proc. Natl. Acad. Sci. USA, 85: 7159–7163, 1988; Furchgott R. E., Handbook of Experimental Pharmacology—New Series, 283–335, 1972; Michel M. C. et al., Brit. J. Pharmacol. 111: 533–538, 1994; Schwinn D. A. et al., J. Biol. Chem 265: 8183–8189, 1990; Testa R. et al., Eur. J. Pharmacol. 249: 307–315, 1993.

(2) 5HT$_{1A}$-serotonergic receptor: using the specific ligand $^3$H-8-OH-DPAT according to Fargin et al., Nature 335: 358–360, 1988; Kobilka B. K. et al., Nature 329: 75–79, 1987; Cullen B. R., Meth. Enzym 152: 684–704, 1987; Gozlan, H. et al., J. Receptor Res. 7: 195–221, 1987).

The $\alpha_{1L}$-adrenergic receptor is not yet cloned and, therefore, the functional affinity of the compounds of the invention for this subtype can be assessed by using an isolated organ preparation as reported by Testa et al., J. Pharmacol. Exp. Ther. 281: 1284–1293, 1997; Oshita, M. et al., Br. J. Pharmacol. 108: 1071–1076, 1993.

In vitro testing of the compounds of this invention on the above receptors is described in Examples 37 and 38 below.

The drugs having $\alpha_1$-adrenergic antagonistic activity currently used for the symptomatic therapy of BPH are poorly subtype selective and subject to cause relevant side effects due to their hypotensive activity.

Thus there is a need for selective $\alpha_1$-antagonists which do not subject the BPH patient to the side effects, especially the cardiovascular side effects of said treatment. The very high uroselectivity of the compounds of this invention has been tested in the dog model described in Example 39, where their efficacy in antagonizing the contractions of prostatic urethra in the presence of very limited effects on blood pressure has been shown, in comparison to compound A and to another well-known $\alpha_1$-antagonist, prazosin.

SYNTHESIS OF COMPOUNDS OF THE INVENTION

The compounds according to the invention may generally be prepared as follows.

Alternatively, the condensation can be carried out without a solvent at 150–220° C. (Mitchell et al., J. Am. Chem. Soc., 53:1879, 1931) or in high-boiling ethereal solvents (e.g., diglyme).

The condensation can be also performed through preparation and optional isolation of reactive derivatives of 1, such as acyl halides. Formation of acyl halides of compounds of formula 1 and reactions with amines 2 to form amides is well documented in the literature and known to people skilled in the art.

Also less reactive derivatives of 1 can be used, such as alkyl esters, which, in turn, can be converted into 1 in the presence of a condensing agent (e.g., trimethylaluminum) in an aprotic and/or a chlorinated solvent (e.g., hexane, dichloromethane) at −10/80° C., or without solvents at Scheme 1

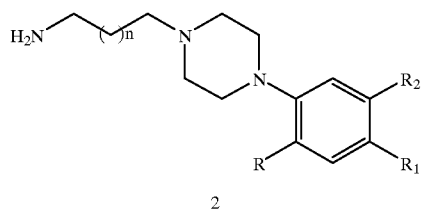

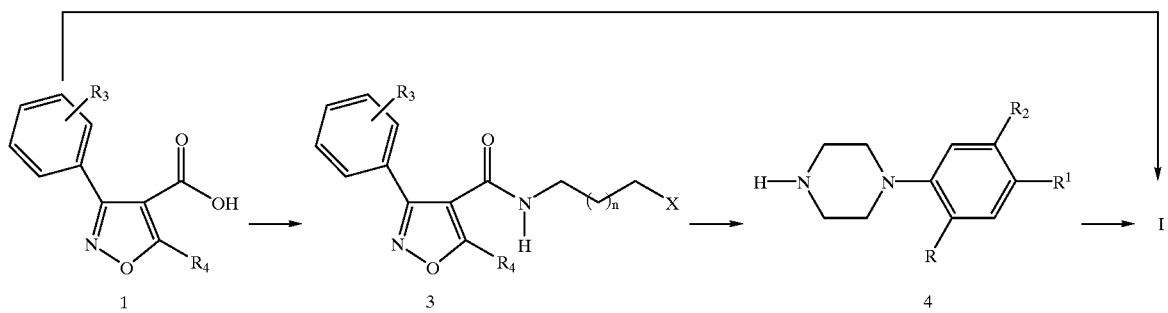

Direct condensation of compounds 1, 4-carboxy-3-aryl isoxazole derivatives, with the ω-aminoalkyl derivatives 2 (Scheme 1) leads to the compounds of the invention. The condensation can be carried out in presence of a condensing agent (e.g., dicyclohexylcarbodiimide or diethyl cyanophosphonate) optionally in the presence of a promoting agent (e.g., N-hydroxysuccinimide, 4-dimethylaminopyridine or N,N'-carbonyldiimidazole) in an aprotic or chlorinated solvent (e.g., dimethylformamide or chloroform) at −10/140° C. (Albertson, Org. React., 12:205–218, 1962; Doherty et al., J. Med. Chem., 35:2–14, 1992; Ishihara et al., Chem. Pharm. Bull., 39:3236–3243, 1991). In some cases the activated intermediate esters or amides (such as O-(N-succinimidyl)esters or acyl imidazolides) can be isolated and further reacted with 2 to be transformed into the corresponding amides (I) in an aprotic or chlorinated solvent at 10/100° C. This kind of condensation is well illustrated in the examples. Another activated intermediate which can be used is the mixed anhydride of 1, obtainable by reacting 1 with an alkyl chloroformate in presence of a tertiary amine (e.g., triethylamine or N-methylmorpholine), then reacted with 2 at 0–80° C.; optionally a promoting agent (e.g., 1-hydroxypiperidine) may be added before the amine addition (Albertson, Org. React., 12:157, 1962).

80–180° C., (Weinreb et al., Tetrahedron Lett., 4171, 1977; Lipton et al., Org. Synth., 59:49, 1979).

By the same methods of condensation reported above and using $H_2NCH_2(CH_2)_nCH_2X$ (with X=halogen or OH) as a reagent, 1 can be transformed into 3. In the case of X=OH, the alcoholic group is then converted into a suitable leaving group by methods well known to those skilled in the art. Compounds 3 (with X=leaving group such as halogen or aryl/alkylsulphonyloxy group) can be subsequently reacted with an appropriate phenylpiperazine 4 bearing the desired phenyl group. The nucleophilic substitution is carried out preferably, but not necessarily at a temperature within the range of 20–200° C. in a polar solvent such as dimethylformamide, acetonitrile or methanol, or without any solvent, usually in the presence of a base such as potassium carbonate. See also Gibson's chapter in Patai: "The Chemistry of the Amino Group", p. 45, Wiley Int. Sci., N.Y. (1968).

The preparation of compounds 1 which are not commercially available is disclosed in the literature and is well known to those skilled in the art and is usually carried out performing 1,3-dipolar cycloaddition reactions on benzohydroxamoyl halides (usually prepared by halogenation reaction on properly substituted benzaldoximes with elemental halides or alkali hypohalogenides or N-chloro-(or bromo) succinimide) with β-ketoesters or alkyl β-aminoacrylates ($R_4$=H) or alkyl propiolates in alkaline condition in a proper solvent (e.g., dimethylformamide, ethanol, diethyl ether, chlorinated solvents at a temperature in the range between −20° C. to reflux, usually carrying out the reactions at 20–30° C.). (Scheme 2) See *J. Chem. Soc.* 19063, 5838–5845 and 5845–5854; *J. Am. Chem. Soc.* 1985, 107, 2721–2730, *J. Agric. Food Chem.* 1995, 43, 219–228; U.S. Pat. No. 4,144,047.

standard phthalimido-group deprotection and the reduction of the amido or cyano group provide compounds 2.

The compounds I where R is a trifluoromethanesulphonyloxy group can be synthesised starting from compounds I where R is a hydroxy group by known procedures that include the use of trifluoromethanesulphonic anhydride or N-phenyltrifluoromethanesulphonimide in aprotic solvents such as, for example, 1,2-dichloroethane or other chlori- Scheme 2

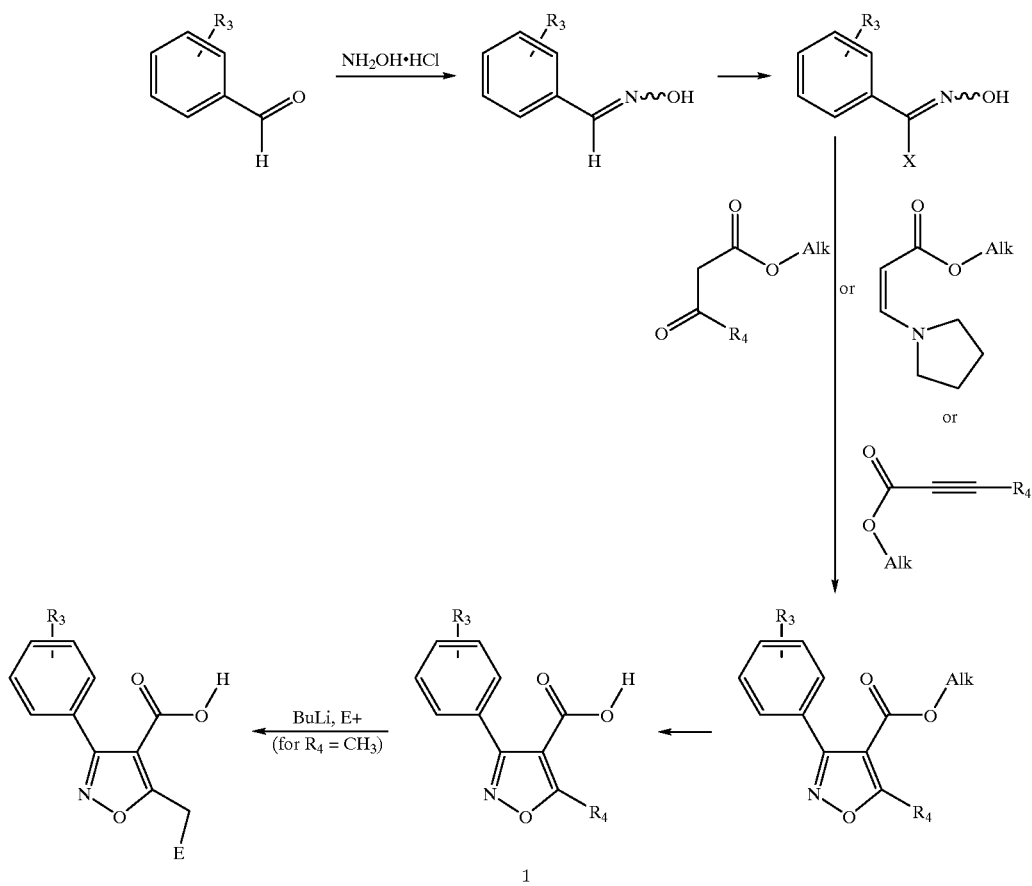

Variation of the $R_4$ substitution can be obtained by using properly substituted β-ketoesters or alkyl propiolates or by reacting the lithium carbanion of the methyl derivatives 1 ($R_4$=CH$_3$) with various electrophiles in aprotic solvents such as tetrahydrofuran, diethyl ether, benzene, toluene or others at a temperature between −78° C. and the temperature of reflux of the solvent (*J. Org. Chem.* 1985, 50, 5660–5666; *J. Med. Chem.* 1988, 31, 473–476; *J. Med. Chem.* 1990, 33, 2255–2259). The carboxylic functionality can be protected or not.

The preparation of compounds 2 is disclosed in the literature and is well known to those skilled in the art, and includes nucleophilic substitution of a phenylpiperazine 4 on a N-(ω-haloalkyl)phthalimide or a proper ω-haloalkylnitrile or amide by the method illustrated above for the condensation of compounds 3 and 4 or by addition of a α,β-unsaturated alkylnitrile or amide in a suitable solvent (e.g., acetonitrile, dimethylformamide, a chlorinated solvent or other aprotic polar solvent) at a temperature between 0° C. and the reflux temperature of the solvent. The following nated solvents, toluene at a temperature in the range between −20° C. and the reflux temperature of the solvent (Hendickson et al., Tetrahedron Letters, 4607, 1973).

The N-oxides of compounds I may be synthesised by simple oxidation procedures known to those skilled in the art. The oxidation procedure described by Brougham, Synthesis, 1015–1017, 1987, allows differentiation of the two nitrogen atoms of the piperazine ring, permitting both the N-oxides and the N,N'-dioxide to be obtained.

The preparation of the phenylpiperazines 4, not yet known in the literature, is very well documented in the experimental part and uses synthetic procedures very well known to those skilled in the art, which comprise the synthesis of the proper aniline through standard reactions and the subsequent cyclization with bis-(2-chloroethylamine) to afford the piperazine following the method of Prelog et al., Collect. Czech. Chem. Comm., 5:497–502, 1933 or its variations (Elworthy, J. Med. Chem., 40:2674–2687, 1997).-

Representative examples of the compounds of the invention are, with no intention to limit:

3-phenyl-N-{3-[4-(2-methoxyphenyl)-1-piperazinyl]propyl}isoxazole-4-carboxamide;
3-phenyl-N-{3-[4-(2-hydroxyphenyl)-1-piperazinyl]propyl}isoxazole-4-carboxamide;
3-phenyl-N-{3-[4-(5-fluoro-2-methoxyphenyl)-1-piperazinyl]propyl}isoxazole-4-carboxamide;
3-phenyl-N-{3-[4-(5-fluoro-2-hydroxyphenyl)-1-piperazinyl]propyl}isoxazole-4-carboxamide;
5-methyl-3-phenyl-N-{3-[4-(2-methoxyphenyl)-1-piperazinyl]propyl}isoxazole-4-carboxamide;
5-methyl-3-phenyl-N-{3-[4-(2-hydroxyphenyl)-1-piperazinyl]propyl}isoxazole-4-carboxamide;
5-methyl-3-phenyl-N-{3-[4-(5-fluoro-2-methoxyphenyl)-1-piperazinyl]propyl}isoxazole-4-carboxamide;
5-methyl-3-phenyl-N-{3-[4-(2-methoxy-4-fluorophenyl)-1-piperazinyl]propyl}isoxazole-4-carboxamide;
5-methyl-3-phenyl-N-{3-[4-(2-hydroxy-4-fluorophenyl)-1-piperazinyl]propyl}isoxazole-4-carboxamide;
5-ethyl-3-phenyl-N-{3-[4-(2-methoxyphenyl)-1-piperazinyl]propyl}isoxazole-4-carboxamide;
5-ethyl-3-phenyl-N-{3-[4-(2-hydroxyphenyl)-1-piperazinyl]propyl}isoxazole-4-carboxamide;
5-ethyl-3-phenyl-N-{3-[4-(5-fluoro-2-methoxyphenyl)-1-piperazinyl]propyl}isoxazole-4-carboxamide; and
5-ethyl-3-phenyl-N-{(3-[4-(4-fluoro-2-methoxyphenyl)-1-piperazinyl]propyl)}isoxazole-4-carboxamide.

DETAILED SYNTHESIS

Below are representative examples intended only to illustrate the invention so as described in the text, with no intention to limit it.

EXAMPLE 1

N-{3-[4-(5-Chloro-2-methoxyphenyl)-1-piperazinyl]propyl}-5-methyl-3-phenylisoxazole-4-carboxamide a) 1-(5-Chloro-2-methoxphenyl)-4-[3-(N-phthalimido)propy]piperazine (Compound 1A)

A mixture of 28.64 g of 1-(5-chloro-2-methoxyphenyl) piperazine, 44.6 g of anhydrous potassium carbonate and 33.65 g of N-(3-bromopropyl)phthalimide in 250 mL of acetonitrile was stirred at reflux for 8 hours. After cooling to room temperature, 800 mL of water was added under stirring and the resulting suspension was filtered by suction yielding a yellowish solid, which was washed with 300 mL of water and crystallized from methanol affording 46.5 g (91%) of the title compound, melting at 131–133° C.

$^1$H-NMR (200 MHz) spectrum; Solvent: CDCl$_3$; Chemical shift (δ)

| | | | |
|---|---|---|---|
| 7.78–7.82 | m | 2H | phthalimide H3, H6 |
| 7.64–7.78 | m | 2H | phthalimide H4, H5 |
| 6.92 | dd | 1H | methoxyphenyl H4 |
| 6.65–6.78 | m | 2H | methoxyphenyl H3, H6 |
| 3.81 | s | 3H | CH$_3$O |
| 3.71–3.89 | m | 2H | CH$_2$N(CO)$_2$ |
| 2.78–3.00 | m | 4H | 2 piperazine CH$_2$s |
| 2.40–2.65 | m | 6H | 2 piperazine CH$_2$s, CH$_2$CH$_2$CH$_2$N(CO)$_2$ |
| 1.80–2.03 | m | 2H | CH$_2$C$\underline{H}_2$CH$_2$ | b) 1-(3-Aminopropyl)-4-(5-chloro-2-methoxyphenyl)piperazine trihydrochloride.2.15 H$_2$O (Compound 1B)

A solution of 20.7 g of Compound 1A and 8.6 mL of 85% hydrazine hydrate in 300 mL of 95% ethanol was stirred at reflux for 3.5 hours. Afterwards, the reaction mixture was cooled to room temperature, diluted with 400 mL of water, acidified with 37% hydrochloric acid (pH=1) and stirred for 0.5 hours. The precipitated solid was collected by filtration and washed with 1N hydrochloric acid followed by water. The filtrate was concentrated by evaporation in vacuo, filtered, made basic by the addition of 35% sodium hydroxide at 0–5° C. and extracted with diethyl ether. The organic layer was washed with brine, dried on sodium sulphate and evaporated to dryness in vacuo affording 13.6 g (96%) of the title compound as a base. Acidification of a solution of the base in chloroform with more than three equivalents of 3N ethanolic hydrogen chloride, followed by evaporation to dryness in vacuo and crystallisation of the residue from ethanol/diethyl ether 10:3 yielded the title compound, melting at 200–202° C.

$^1$H-NMR (200 MHz) spectrum; Solvent: CDCl$_3$; Chemical shift (δ)

| | | | |
|---|---|---|---|
| 11.20–11.50 | br | 1H | NH$^+$ |
| 8.10–8.40 | br | 3H | NH3$^+$ |
| 6.85–7.10 | m | 3H | phenyl H3, H4, H6 |
| 5.10 | br | 5.3H | NH$^+$, 2.15 H$_2$O |
| 3.79 | s | 3H | CH$_3$O |
| 3.35–3.65 | m | 4H | 2 piperazine CH$_2$s |
| 3.03–3.35 | m | 6H | 2 piperazine CH$_2$s, CH$_2$CH$_2$C$\underline{H}_2$NH$_3{}^+$ |
| 2.80–3.03 | m | 2H | C$\underline{H}_2$CH$_2$CH$_2$NH$_3{}^+$ |
| 1.95–2.22 | m | 2H | CH$_2$C$\underline{H}_2$CH$_2$NH$_3{}^+$ | c) N-{3-[4-(5-Chloro-2-methoxyphenyl)-1-piperazinyl]propyl}-5-methyl-3-phenylisoxazole-4-carboxamide 1.08 g of 93% diethyl cyanophosphonate and 0.92 mL of triethylamine were added to a mixture of 1.22 g of 3-phenyl-5-methylisoxazole-4-carboxylic acid, 1.87 g of Compound 1B as its base and 30 mL of anhydrous dimethylformamide stirred at 0–5° C. The temperature was allowed to rise to 20–25° C. and, after 3.5 hours' stirring, the mixture was poured into 300 mL of water and extracted with ethyl acetate. The combined organic layers were washed with 5% aqueous sodium carbonate and water. After drying on sodium sulphate, the solvent was removed in vacuo. The crude was crystallized from ethanol to yield 2.11 g (75%) of the title compound, melting at 139–142° C.

$^1$H-NMR (200 MHz) spectrum; Solvent: CDCl$_3$; Chemical shift (δ)

| | | | |
|---|---|---|---|
| 7.60–7.70 | m | 2H | phenyl H2, H6 |
| 7.45–7.55 | m | 3H | phenyl H3, H4, H5 |
| 6.95 | dd | 1H | methoxyphenyl H4 |
| 6.85 | d | 1H | methoxyphenyl H6 |
| 6.75 | d | 1H | methoxyphenyl H3 |
| 6.25 | t | 1H | NH |
| 3.82 | s | 3H | OCH$_3$ |
| 3.40 | q | 2H | NHC$\underline{H}_2$ |
| 2.80–2.95 | m | 4H | 2 piperazine CH$_2$s |
| 2.69 | s | 3H | CH$_3$ |
| 2.40–2.55 | m | 4H | 2 piperazine CH$_2$s |
| 2.30 | t | 2H | CONHCH$_2$CH$_2$C$\underline{H}_2$N |
| 1.55–1.70 | m | 2H | CH$_2$C$\underline{H}_2$CH$_2$ |

EXAMPLE 2

N-{3-[4-(5-Chloro-2-hydroxyphenyl)-1-piperazinyl]propyl}-5-methyl-3-phenylisoxazole-4-carboxamide a) 1-(5-Chloro-2-hydroxyphenyl)piperazine dihydrobromide (Compound 2A)

A suspension of 5.5 g of 1-(5-chloro-2-methoxyphenyl) piperazine in 40 mL of 62% hydrobromic acid was stirred at reflux for 30 hours. After cooling to room temperature, the mixture was filtered by suction and the solid was washed on the funnel with acetone affording 6.02 g of the title compound. M.p.>270° C. (ethanol).

$^1$H-NMR (200 MHz) spectrum; Solvent: CDCl$_3$; Chemical shift (δ)

| | | | |
|---|---|---|---|
| 9.35–9.80 | br | 2H | NH$_2$$^+$ |
| 8.60–9.05 | br | 2H | NH$^+$, OH |
| 6.70–6.97 | m | 3H | aromatic CHs |
| 3.00–3.38 | m | 8H | piperazine CH$_2$s | b) N-(3-Chloropropyl)-3-phenyl-5-methylisoxazole-4-carboxamide (Compound 2B)

The title compound was synthesised following the procedure described for the compound of Example 1c, but substituting 3-chloropropylamine hydrochloride for Compound 1B and doubling the amount of triethylamine. Pouring the reaction mixture into iced water and filtering the precipitated solid, which was washed on the funnel with a 2:1 water:dimethylformamide mixture followed by water, afforded, after drying, the pure title compound. M.p. 122–124° C.

$^1$H-NMR (200 MHz) spectrum; Solvent: CDCl$_3$; Chemical shift (δ)

| | | | |
|---|---|---|---|
| 7.45–7.60 | m | 5H | phenyl CHs |
| 5.50 | br | 1H | NH |
| 3.30–3.45 | m | 4H | C$\underline{H}_2$CH$_2$C$\underline{H}_2$ |
| 2.70 | s | 3H | CH$_3$ |
| 1.80–1.90 | m | 2H | CH$_2$C$\underline{H}_2$CH$_2$ | c) N-{3-[4-(5-Chloro-2-hydroxyohenyl)-1-piperazinyl]propyl}-5-methyl-3-phenylisoxazole-4-carboxamide A mixture of 0.28 g of Compound 2B, 0.21 g of Compound 2A and 0.14 g of potassium carbonate was heated at 160° C. for 20 minutes. After cooling to room temperature, the mixture was taken up with 8 mL of chloroform, and inorganic matter was filtered off. The filtrate was evaporated to dryness and purified by flash chromatography (chloroform:methanol 97.5:2.5) to yield 0.32 g (71%) of the title compound. M.p. 92–98° C.

$^1$H-NMR (200 MHz) spectrum; Solvent: CDCl3; Chemical shift (δ)

| | | | |
|---|---|---|---|
| 7.60–7.75 | m | 2H | phenyl H2, H6 |
| 7.45–7.60 | m | 3H | phenyl H3, H4, H5 |
| 7.00–7.10 | m | 2H | hydroxyphenyl H4, H6 |
| 6.85 | d | 1H | hydroxyphenyl H3 |
| 6.70 | br | 1H | OH |
| 6.02 | t | 1H | NH |
| 3.35 | q | 2H | NHC$\underline{H}_2$ |
| 2.62–2.75 | m | 7H | 2 piperazine CH$_2$s and CH$_3$ |
| 2.38–2.50 | m | 4H | 2 piperazine CH$_2$s |
| 2.30 | t | 2H | CONHCH$_2$CH$_2$C$\underline{H}_2$N |
| 1.55–1.70 | m | 2H | CH$_2$C$\underline{H}_2$CH$_2$ |

EXAMPLE 3

5-Methyl-3-phenyl-N-{3-[4-[2-(2,2,2-trifluoroethoxy)phenyl]-1-piperazinyl]propyl}isoxazole-4-carboxamide This compound was prepared as described in Example 2c, substituting 1-[2-(2,2,2-trifluoroethoxy)phenyl]piperazine (prepared as described in European patent EP 748800, Bantle et al.) for Compound 2A. The crude was purified by flash chromatography (ethyl acetate:methanol 95:5) to afford the title compound (47%). M.p. 124–125° C.

$^1$H-NMR (200 MHz) spectrum; Solvent: CDCl$_3$; Chemical shift (δ)

| | | | |
|---|---|---|---|
| 7.60–7.70 | m | 2H | phenyl H2, H6 |
| 7.40–7.55 | m | 3H | phenyl H3, H4, H5 |
| 6.88–7.05 | m | 4H | trifluoroethoxyphenyl CHs |
| 6.35 | t | 1H | NH |
| 4.35 | q | 2H | OCH$_2$CF$_3$ |
| 3.40 | q | 2H | NHC$\underline{H}_2$ |
| 2.80–2.95 | m | 4H | 2 piperazine CH$_2$s |
| 2.65 | s | 3H | CH$_3$ |
| 2.30–2.45 | m | 4H | 2 piperazine CH$_2$s |
| 2.30 | t | 2H | CONHCH$_2$CH$_2$C$\underline{H}_2$N |
| 1.55–1.70 | m | 2H | CH$_2$C$\underline{H}_2$CH$_2$ |

The related compound, 5-methyl-3-phenyl-N-{3-[4-[2-(2,2,2-trifluoroethoxy)phenyl]-1-piperazinyl]propyl}isoxazole-4-carboxamide (2HCl.0.3H$_2$O) can be obtained by usual salification procedure with hydrogen chloride (isopropanol solution). M.p. 176.6–178.7° C. (acetonitrile).

EXAMPLE 4

N-{3-[4-[2-Methoxy-5-(2,2,2-trifluoroethoxy)phenyl]-1-piperazinyl]propyl}-5-methyl-3-phenylisoxazole-4-carboxamide a) 1-(t-Butoxycarbonyl)-4-(5-hydroxy-2-methoxyphenyl)piperazine (Compound 4A)

A solution of 8 g of 1-(5-hydroxy-2-methoxyphenyl) piperazine dihydrobromide (prepared as described in U.S. Pat. No. 5,605,896, Leonardi et al.) and 3.17 g of anhydrous potassium carbonate in 30 mL of water was evaporated to dryness in vacuo. 100 mL of anhydrous tetrahydrofuran and 5.18 g of di-t-butyl dicarbonate (BOC$_2$O) were added to the residue and the mixture was stirred at room temperature for 2 hours, then 100 mL of anhydrous tetrahydrofuran was added. The suspension was filtered and the solvent was removed in vacuo. The residue was dissolved in 200 mL of chloroform, the solution was washed with 3×50 mL of 5% sodium bicarbonate, 2×50 mL of water and dried over sodium sulphate. The solvent was removed at reduced pressure and the residue was purified by flash chromatography (petroleum ether:ethyl acetate 75:25) to give 1.91 g (28.7%) of Compound 4A and 1.58 g (35.7%) of 1-(t-butoxycarbonyl)-4-[5-(t-butoxycarbonyloxy)-2-methoxyphenyl]piperazine. A solution of this by-product, 40 mL of methanol and 6 mL of 1N sodium hydroxide was maintained overnight at room temperature. The mixture was neutralised with acetic acid; the solvent was removed at reduced pressure and the residue dissolved in 40 mL of chloroform. After washing with 3×10 mL of water, the organic layer was dried over sodium sulphate and the solvent evaporated off in vacuo to recover an additional 1.15 g (17.2%) of Compound 4A (total 45.9%).

$^1$H-NMR (200 MHz) spectrum; Solvent: CDCl$_3$; Chemical shift (δ)

| | | | |
|---|---|---|---|
| 6.70 | d | 1H | phenyl H3 |
| 6.45–6.53 | m | 2H | pheny H4, H6 |
| 5.77 | br | 1H | OH |
| 3.78 | s | 3H | $CH_3O$ |
| 3.48–3.68 | m | 4H | 2 piperazine $CH_2$s |
| 2.82–3.05 | m | 4H | 2 piperazine $CH_2$s |
| 1.48 | s | 9H | $(CH_3)_3C$ | b) 1-(t-Butoxycarbonyl)-4-[2-methoxy-5-(2,2,2-trifluoroethoxy)phenyl]piperazine (Compound 4B)

A stirred mixture of 2.83 g of Compound 4A, 6.05 g of cesium carbonate and 2.95 g of 2,2,2-trifluoroethyl p-toluenesulphonate in 60 mL of acetonitrile was refluxed for 16 hours. The solvent was evaporated at reduced pressure. 90 mL of brine was added to the residue and the mixture was extracted with 3×40 mL of ethyl acetate. The organic layer was washed with 3×20 mL of water and 20 mL of brine, and dried over sodium sulphate. The solvent was removed at reduced pressure and the residue purified by flash chromatography (petroleum ether/ethyl acetate gradient 95:5 to 80:20). The solvents were removed in vacuo to give 1.86 g (52%) of Compound 4B as a white solid. M.p. (98) 102–105° C.

$^1$H-NMR (200 MHz) spectrum; Solvent: $CDCl_3$; Chemical shift ($\delta$)

| | | | |
|---|---|---|---|
| 6.77 | d | 1H | phenyl H3 |
| 6.45–6.63 | m | 2H | phenyl H4, H6 |
| 4.28 | q | 2H | $CF_3CH_2O$ |
| 3.84 | s | 3H | $CH_3O$ |
| 3.53–3.68 | m | 4H | 2 piperazine $CH_2$s |
| 2.90–3.06 | m | 4H | 2 piperazine $CH_2$s |
| 1.48 | s | 9H | $(CH_3)_3C$ | c) 1-[2-Methoxy-5-(2,2,2-trifluoroethoxy)phenyl]piperazine.1.9 HCl (Compound 4C)

A solution of 2.42 mL of trifluoroacetic acid in 30 mL of anhydrous dichloromethane was added dropwise at 3–5° C. to a stirred solution of 1.17 g of Compound 4B in 40 mL of anhydrous dichloromethane. The mixture was maintained overnight at room temperature, washed with 2×30 mL of 2N sodium hydroxide and extracted with 3×15 mL of 2N hydrochloric acid. The aqueous acid layer was washed with 2×20 mL of diethyl ether, alkalinised with 37% sodium hydroxide at 5–10° C. and extracted with 3×30 mL of diethyl ether. The organic layer was dried over sodium sulphate and the solvent was removed in vacuo to give 0.78 g (89%) of compound 4C base as a thick oil. A solution of this base in diethyl ether was treated with charcoal, filtered and acidified by addition of 3.6N hydrogen chloride in diethyl ether to give the hydrochloride salt, recovered by filtration and crystallised from acetonitrile and ethanol (7.5:1) to yield the analytical sample. M.p. (188) 202–208° C (dec.).

$^1$H-NMR (200 MHz) spectrum; Solvent: $CDCl_3$; Chemical shift ($\delta$)

| | | | |
|---|---|---|---|
| 9.18 | br | 1.9H | $NH_2^+$ |
| 6.90 | d | 1H | phenyl H3 |
| 6.67 | dd | 1H | phenyl H4 |
| 6.59 | d | 1H | phenyl H6 |
| 6.11 | br | 1H | $NH^+$ |
| 4.66 | q | 2H | $CF_3CH_2O$ |
| 3.74 | s | 3H | $CH_3O$ |
| 3.18 | br | 8H | piperazine $CH_2$s | d) N-{3-[4-[2-Methoxy-5-(2,2,2-trifluoroethoxy)phenyl]-1-piperazinyl]propyl}-5-methyl-3-phenylisoxazole-4-carboxamide This compound was prepared as described in Example 2c, but substituting Compound 4C for Compound 2A. After cooling to room temperature, the crude was purified by flash chromatography (dichloromethane:2N ammonia in methanol 97.5:2.5) to afford the title compound (54%). M.p. 125° C.

$^1$H-NMR (200 MHz) spectrum; Solvent: $CDCl_3$; Chemical shift ($\delta$)

| | | | |
|---|---|---|---|
| 7.65–7.75 | m | 2H | phenyl H2, H6 |
| 7.45–7.55 | m | 3H | phenyl H3, H4, H5 |
| 6.75 | d | 1H | trifluoroethoxyphenyl H3 |
| 6.45–6.55 | m | 2H | trifluoroethoxyphenyl H4, H6 |
| 6.20 | t | 1H | NH |
| 4.30 | q | 2H | $OCH_2CF_3$ |
| 3.80 | s | 3H | $OCH_3$ |
| 3.35 | q | 2H | $NHC\underline{H}_2$ |
| 2.80–2.95 | m | 4H | 2 piperazine $CH_2$s |
| 2.65 | s | 3H | $CH_3$ |
| 2.35–2.48 | m | 4H | 2 piperazine $CH_2$s |
| 2.27 | t | 2H | $CONHCH_2CH_2C\underline{H}_2N$ |
| 1.52–1.68 | m | 2H | $CH_2C\underline{H}_2CH_2$ |

EXAMPLE 5

N-{3-[4-[5-Fluoro-2-(2,2,2-trifluoroethoxy)phenyl]-1-piperazinyl]propyl}-5-methyl-3-phenylisoxazole-4-carboxamide a) 5-Fluoro-2-(2,2,2-trifluoroethoxy)nitrobenzene (Compound 5A)

A stirred mixture of 3.14 g of 4-fluoro-2-nitrophenol, 13 g of cesium carbonate and 20 mL of anhydrous dimethylformamide was heated at 100° C. for 4 hours. After this period, 6.65 g of 2,2,2-trifluoroethyl p-toluenesulphonate was added and the mixture was stirred at the same temperature for 40 hours. Afterwards, the solvent was removed under reduced pressure at 35° C. and 50 mL of water was added to the residue. The mixture was acidified with 37% hydrochloric acid and extracted with 3×40 mL of ethyl acetate. The organic layer was washed with 20 mL of brine, dried over sodium sulphate and evaporated to dryness in vacuo. The residue was purified by flash chromatography (petroleum ether:ethyl acetate 100:7) to afford 1.53 g (32%) of Compound 5A as an oil.

$^1$H-NMR (200 MHz) spectrum; Solvent: $CDCl_3$; Chemical shift ($\delta$)

| | | | |
|---|---|---|---|
| 7.65 | dd | 1H | H6 |
| 7.32 | ddd | 1H | H4 |
| 7.16 | dd | 1H | H3 |
| 4.42 | q | 2H | CH$_2$ | b) 5-Fluoro-2-(2,2,2-trifluoroethoxy)aniline (Compound 5B)

A mixture of 0.66 g of Compound 5A and 0.07 g of Raney-Nickel in 20 mL of ethyl acetate was stirred for 14 hours at 20–25° C. The organic layer was separated and the mixture extracted with 2×40 mL of ethyl acetate. The combined organic layers were washed with 20 mL of brine, dried over sodium sulphate and evaporated to dryness in vacuo to afford 0.52 g (90.6%) of Compound 5B as an orange oil.

$^1$H-NMR (200 MHz) spectrum; Solvent: CDCl$_3$; Chemical shift (δ)

| | | | |
|---|---|---|---|
| 6.70 | dd | 1H | H6 |
| 6.28–6.50 | m | 2H | H3 and H4 |
| 4.32 | q | 2H | CH$_2$ |
| 3.92 | br | 2H | NH$_2$ | c) 1-[5-Fluoro-2-(2,2,2-trifluoroethoxy)phenl] piperazine (Compound 5C)

A stirred mixture of 0.52 g of Compound 5B, 0.45 g of bis-(2-chloroethyl)amine hydrochloride, 0.5 g of potassium iodide, 0.34 g of anhydrous potassium carbonate and 20 mL of n-butanol was refluxed for 32 hours under nitrogen. The solvent was removed under reduced pressure. The residue was treated with 10 mL of water and 10 mL of 20% aqueous sodium carbonate and extracted with 2×30 mL of ethyl acetate. The organic layer was washed with brine, dried over sodium sulphate and evaporated to dryness in vacuo. The residue was purified by flash chromatography (chloroform:2N ammonia in methanol gradient from 100:3 to 100:5) to afford 0.1 g (14%) of Compound 5C as an oil.

$^1$H-NMR (200 MHz) spectrum; Solvent: CDCl$_3$; Chemical shift (δ)

| | | | |
|---|---|---|---|
| 6.80–6.93 | m | 1H | H3 |
| 6.55–6.71 | m | 2H | H6, H4 |
| 4.36 | q | 2H | OCH$_2$CF$_3$ |
| 3.05 | br | 8H | piperazine CH$_2$s |
| 2.38 | s | 1H | NH | d) N-{3-[4-[5-Fluoro-2-(2,2,2-trifluoroethoxy)phenyl]-1-piperazinyl]propyl}-5-methyl-3-phenylisoxazole-4-carboxamide This compound was prepared as described in Example 2c, substituting Compound 5C for Compound 2A. After cooling to room temperature, the crude was purified by flash chromatography (dichloromethane:2N ammonia in methanol 97.5:2.5) to afford the title compound (59%). M.p. 123–125° C.

$^1$H-NMR (200 MHz) spectrum; Solvent: CDCl$_3$; Chemical shift (δ)

| | | | |
|---|---|---|---|
| 7.60–7.70 | m | 2H | phenyl H2, H6 |
| 7.45–7.55 | m | 3H | phenyl H3, H4, H5 |
| 6.80–6.90 | m | 1H | trifluoroethoxyphenyl H3 |
| 6 55–6.70 | m | 2H | trifluoroethoxyphenyl H4, H6 |
| 6.20 | t | 1H | NH |
| 4.30 | q | 2H | OCH$_2$CF$_3$ |
| 3.35 | q | 2H | NHC$\underline{H}_2$ |
| 2.80–2.95 | m | 4H | 2 piperazine CH$_2$s |
| 2.65 | s | 3H | CH$_3$ |
| 2.35–2.45 | m | 4H | 2 piperazine CH$_2$s |
| 2.25 | t | 2H | CONHCH$_2$CH$_2$C$\underline{H}_2$N |
| 1.50–1.65 | m | 2H | CH$_2$C$\underline{H}_2$CH$_2$ |

EXAMPLE 6

N-{3-[4-[4-Fluoro-2-(2,2,2-trifluoroethoxy)phenyl]-1-piperazinyl]propyl}-5-methyl-3-phenylisoxazole-4-carboxamide This compound was prepared as described in Example 2, substituting 1-[4-fluoro-2-(2,2,2-trifluoroethoxy)phenyl] piperazine (prepared as described in European patent EP 748800, Bantle et al.) for Compound 2A. After cooling to room temperature, the crude was purified by flash chromatography (dichloromethane:2N ammonia in methanol 98:2) to afford the title compound (64%). M.p. 112–135° C°.

$^1$H-NMR (200 MHz) spectrum; Solvent: CDCl$_3$; Chemical shift (δ)

| | | | |
|---|---|---|---|
| 7.60–7.70 | m | 2H | phenyl H2, H6 |
| 7.45–7.55 | m | 3H | phenyl H3, H4, H5 |
| 6.60–6.85 | m | 3H | trifluoroethoxyphenyl H3, H5, H6 |
| 6.28 | t | 1H | NH |
| 4.20–4.40 | m | 2H | OCH$_2$CF$_3$ |
| 3.35 | q | 2H | NHC$\underline{H}_2$ |
| 2.75–2.90 | m | 4H | 2 piperazine CH$_2$s |
| 2.65 | s | 3H | CH$_3$ |
| 2.35–2.45 | m | 4H | 2 piperazine CH$_2$s |
| 2.25 | t | 2H | CONHCH$_2$CH$_2$C$\underline{H}_2$N |
| 1.50–1.65 | m | 2H | CH$_2$C$\underline{H}_2$CH$_2$ |

The related compound N-{3-[4-[4-fluoro-2-(2,2,2-trifluoroethoxy)phenyl]-1-piperazinyl]propyl}-5-methyl-3-phenylisoxazole-4-carboxamide monomethanesulphonate can be obtained by usual salification procedure with methanesulphonic acid (ethyl acetate solution). M.p. 190–192° C. (98% aq. isopropanol).

EXAMPLE 7

N-{3-[4-(5-Chloro-2-trifluoromethanesulphonyloxy)-1-piperazinyl] propyl}-5-methyl-3-phenylisoxazole-4-carboxamide 0.07 mL of triethylamine was added at room temperature to a stirred mixture of 0.22 g of the Compound of Example 2, 0.18 g of N-phenyltriflimide and 5 mL of dichloromethane. The mixture was stirred for 10 days; during this period 2 additional amounts of N-phenyltriflimide (0.18 and 0.09 g) and of triethylamine (0.07 and 0.04 mL) were added. The reaction mixture was diluted with 5 mL of dichloromethane, washed with 10% aqueous sodium carbonate, water, dried over sodium sulphate and evaporated to dryness in vacuo. The crude was purified by flash chromatography (ethyl acetate:methanol 95:5) to afford 0.17 g (58%) of the pure title compound. M.p. 49–53° C.

¹H-NMR (200 MHz) spectrum; Solvent: CDCl₃; Chemical shift (δ)

| | | | |
|---|---|---|---|
| 7.65–7.75 | m | 2H | phenyl H2, H6 |
| 7.50–7.60 | m | 3H | phenyl H3, H4, H5 |
| 7.02–7.10 | m | 3H | chlorophenyl H3, H4, H6 |
| 6.20 | t | 1H | NH |
| 3.35 | q | 2H | NHC$\underline{H}_2$ |
| 2.75–2.85 | m | 4H | 2 piperazine CH₂s |
| 2.70 | s | 3H | CH₃ |
| 2.40–2.50 | m | 4H | 2 piperazine CH₂s |
| 2.32 | t | 2H | CONHCH₂CH₂C$\underline{H}_2$N |
| 1.55–1.70 | m | 2H | CH₂C$\underline{H}_2$CH₂ |

EXAMPLE 8

3-(4-Fluorophenyl)-N-[3-[4-[4-fluoro-2-(2,2,2-trifluoroethoxy)phenyl]-1-piperazinyl]propyl]-isoxazole-4-carboxamide a) 1-[4-Fluoro-2-(2,2,2-trifluoroethoxy)phenyl]-4-[3-(N-phthalimido)propyl]piperazine (Compound 8A)

The title compound was synthesised following the procedure described for Compound 1A of Example 1 but substituting 1-[4-fluoro-2-(2,2,2-trifluoroethoxy)phenyl] piperazine for 1-(5-chloro-2-methoxyphenyl)pi-perazine. The reaction mixture was extracted with diethyl ether and the organic solution was dried over sodium sulphate and filtered on silica gel, washing the panel with diethyl ether. Evaporation to dryness in vacuo afforded the title product (66%). M.p. (104) 108–110° C.

¹H-NMR (200 MHz) spectrum; Solvent: CDCl₃; Chemical shift (δ)

| | | | |
|---|---|---|---|
| 7.60–7.95 | m | 4H | phthalimido CHs |
| 6.52–6.90 | m | 3H | fluorophenyl CHs |
| 4.35 | q | 2H | OCH₂CF₃ |
| 3.80 | t | 2H | (CO)₂NC$\underline{H}_2$ |
| 2.70–3.20 | m | 4H | 2 piperazine CH₂s |
| 2.30–2.70 | m | 6H | (CO)₂NCH₂CH₂C$\underline{H}_2$N, 2 piperazine CH₂s |
| 1.75–2.10 | m | 2H | (CO)₂NCH₂C$\underline{H}_2$ | b) 1-(3-Aminopropyl)-4-[4-fluoro-2-(2,2,2-trifluoroethoxy)phenyl]piperazine (Compound 8B)

The title compound was synthesised following the procedure described for Compound 1B of Example 1 but substituting Compound 8A for Compound 1A. Extraction of alkalinised filtrate with dichloromethane afforded the title compound (84.8%) as an oil.

¹H-NMR (200 MHz) spectrum; Solvent: CDCl₃; Chemical shift (δ)

| | | | |
|---|---|---|---|
| 6.82–6.98 | m | 1H | H5 |
| 6.58–6.82 | m | 2H | H3 and H6 |
| 4.38 | q | 2H | OCH₂CF₃ |
| 2.92–3.12 | m | 4H | 2 piperazine CH₂s |
| 2.80–2.92 | m | 2H | H₂NC$\underline{H}_2$CH₂CH₂N |
| 2.40–2.75 | m | 8H | $\underline{H}_2$NCH₂CH₂C$\underline{H}_2$N, 2 piperazine CH₂s |
| 1.62–1.82 | m | 2H | H₂NCH₂C$\underline{H}_2$CH₂N | c) Methyl 3-(4-fluorophenyl)isoxazole-4-carboxylate (Compound 8C)

To a solution of 1.05 g of 4-fluorobenzaldoxime (Beil. 7, I 132d, II 177d, III 863c) in 15 mL of chloroform were added 1.35 g of N-bromosuccinimide (NBS) and 0.04 mL of pyridine; the resulting mixture was stirred at r.t for 4 h under nitrogen atmosphere. After cooling at 0° C., 1.75 g of methyl β-pyrrolidinoacrylate (prepared as described in U.S. Pat. No. 4,144,047) and 1.26 mL of triethylamine were added and the suspension was stirred at r.t. for 18 h. The reaction mixture was diluted with 20 mL of 2 N hydrochloric acid, 20 mL of water; the organic layer was separated, washed again with 2 N hydrochloric acid and water, dried (sodium sulphate), and evaporated to dryness in vacuo. The crude was purified by flash chromatography (toluene-dichloromethane 1:9) to afford the title compound (47%) as an oil.

¹H-NMR (200 MHz) spectrum; Solvent: CDCl₃; Chemical shift (δ)

| | | | |
|---|---|---|---|
| 9.02 | s | 1H | isoxazole H5 |
| 7.71–7.91 | m | 2H | phenyl CHs |
| 7.08–7.27 | m | 2H | phenyl CHs |
| 3.81 | s | 3H | COOCH₃ | d) 3-(4-Fluorophenyl)isoxazole-4-carboxylic acid (Compound 8D)

A mixture of 0.79 g of Compound 8C, 3.5 mL of acetic acid and 3.05 mL of 37% HCl was refluxed for 4 h. After cooling to r.t., the solvent was evaporated to dryness at reduced pressure and the crude was taken up with 15 mL of water. The precipitate was filtered off and dried to give 0.632 g (85.9%) of the title compound. M.p. 170–174° C.

¹H-NMR (200 MHz) spectrum; Solvent: CDCl₃; Chemical shift (δ)

| | | | |
|---|---|---|---|
| 13.11–13.22 | br | 1H | COOH |
| 9.67 | s | 1H | isoxazole H5 |
| 7.70–7.89 | m | 2H | phenyl CHs |
| 7.16–7.42 | m | 2H | phenyl CHs | e) 3-(4-Fluorophenyl)-N-[3-[4-[4-fluoro-2-(2,2,2-trifluoroethoxy)phenyl]-1-piperazinyl]propyl]-isoxazole-4-carboxamide A solution of 0.3 g of Compound 8D in 1.05 mL of thionyl chloride was refluxed for 1 h under N₂ atmosphere. After cooling to r.t., the solvent was evaporated to dryness and the so obtained crude 3-(4-fluorophenyl)isoxazole-4-carbonyl chloride dissolved in 10 mL of chloroform. Afterwards a solution of 0.48 g of Compound 8B and 0.6 mL of triethylamine in 10 mL of chloroform was added and the resulting mixture stirred at r.t. for 18 h. The solvent was washed with water, dried (sodium sulphate), filtered and evaporated in vacuo. The crude was purified by flash chromatography (ethyl acetate-2N ammonia in methanol 95:5) to give 0.607 g (79.8%) of the title compound. M.p.: 122.4–123° C.

¹H-NMR (200 MHz) spectrum; Solvent: CDCl₃; Chemical shift (δ)

| | | | |
|---|---|---|---|
| 8.89 | s | 1H | isoxazole H5 |
| 7.74–7.87 | m | 2H | trifluoroethoxyphenyl CHs |
| 7.28–7.41 | br | 1H | NH |
| 7.09–7.26 | m | 2H | fluorophenyl CHs |

| | | | |
|---|---|---|---|
| 6.71–6.91 | m | 2H | fluorophenyl CHs |
| 6.59–6.71 | m | 1H | trifluoroethoxyphenyl CH |
| 4.39 | q | 2H | OCH$_2$CF$_3$ |
| 3.50 | q | 2H | NHC$\underline{H}_2$ |
| 2.83–3.01 | m | 4H | 2 piperazine CH$_2$s |
| 2.48–2.72 | m | 6H | CONHCH$_2$CH$_2$C$\underline{H}_2$N and 2 piperazine CH$_2$s |
| 1.80 | q | 2H | CH$_2$C$\underline{H}_2$CH$_2$ |

EXAMPLE 9

3-(2-Chloro-6-fluorophenyl)-N-[3-[4-[4-fluoro-2-(2,2,2-trifluoroethoxy)phenyl]-1-piperazinyl]-propyl]-5-methylisoxazole-4-carboxamide The title compound was synthesised following the procedure described in Example 8, but substituting commercial 3-(2-chloro-6-fluorophenyl)-5-methylisoxazole-4-carbonyl chloride for the crude 3-(4-fluorophenyl)isoxazole-4-carbonyl chloride. Purification by flash chromatography (chloroform-2 N ammonia in metanol 100:3) afforded the title compound (67.5%) as a vitreous solid.

$^1$H-NMR (200 MHz) spectrum; Solvent: CDCl$_3$; Chemical shift (δ)

| | | | |
|---|---|---|---|
| 7.30–7.60 | m | 2H | chlorophenyl H3 and H5 |
| 7.10–7.30 | m | 1H | chlorophenyl H4 |
| 6.58–6.98 | m | 3H | fluorophenyl H3, H5 and H6 |
| 5.80–6.55 | br | 1H | NH |
| 4.38 | q | 2H | OCH$_2$CF$_3$ |
| 3.25–3.50 | m | 2H | NHC$\underline{H}_2$ |
| 2.90–3.25 | m | 4H | 2 piperazine CH$_2$s |
| 2.30–2.90 | m | 9H | CONHCH$_2$CH$_2$C$\underline{H}_2$, CH$_3$, 2 piperazine CH$_2$s |
| 1.40–1.95 | m | 2H | CH$_2$C$\underline{H}_2$CH$_2$ |

EXAMPLE 10

3-(2,6-Dichlorophenyl)-N-[3-[4-[4-fluoro-2-(2,2,2-trifluoroethoxy)phenyl]-1-piperazinyl]propyl]-5-methylisoxazole-4-carboxamide The title compound was synthesised according to the procedure described in Example 1, but using 3-(2,6-dichlorophenyl)-5-methylisoxazole-4-carboxylic acid instead of 3-phenyl-5-methyl-isoxazole-4-carboxylic acid and Compound 8B instead of Compound 1B. Extraction with diethyl ether followed by purification by flash chromatography (chloroform-2 N ammonia in methanol 100:3) afforded the title compound (38%) as an oil.

$^1$H-NMR (200 MHz) spectrum; Solvent: CDCl$_3$; Chemical shift (δ)

| | | | |
|---|---|---|---|
| 7.35–7.58 | m | 3H | dichlorophenyl H3, H4 and H5 |
| 6.58–6.93 | m | 4H | fluorophenyl H3, H5 and H6 |
| 5.35–5.72 | br | 1H | NH |
| 4.38 | q | 2H | OCH$_2$CF$_3$ |
| 3.22–3.42 | m | 2H | NHC$\underline{H}_2$ |
| 2.90–3.10 | m | 4H | 2 piperazine CH$_2$s |
| 2.80 | s | 3H | CH$_3$ |
| 2.40–2.65 | m | 4H | 2 piperazine CH$_2$s |
| 2.15–2.35 | m | 2H | CONHCH$_2$CH$_2$C$\underline{H}_2$N |
| 1.45–1.80 | m | 2H | CH$_2$C$\underline{H}_2$CH$_2$ |

EXAMPLE 11

3-(2-Chlorophenyl)-N-[3-[4-[4-fluoro-2-(2,2,2-trifluoroethoxy)phenyl]-1-piperazinyl]propyl]-5-methylisoxazole-4-carboxamide The title compound was synthesised following the procedure described in Example 8, but substituting commercial 3-(2-chlorophenyl)-5-methylisoxazole-4-carbonyl chloride for the crude 3-(4-fluorophenyl)isoxazole-4-carbonyl chloride. Purification by flash chromatography (chloroform-2 N ammonia in metanol 100:3) afforded the title compound (78.4%) as a vitreous solid.

$^1$H-NMR (200 MHz) spectrum; Solvent: CDCl$_3$; Chemical shift (δ)

| | | | |
|---|---|---|---|
| 7.38–7.62 | m | 4H | chlorophenyl CHs |
| 6.55–6.95 | m | 3H | fluorophenyl CHs |
| 5.40–5.80 | br | 1H | NH |
| 4.35 | q | 2H | OCH$_2$CF$_3$ |
| 3.15–3.60 | m | 2H | NHC$\underline{H}_2$ |
| 2.82–3.15 | m | 4H | 2 piperazine CH$_2$s |
| 2.78 | s | 3H | CH$_3$ |
| 2.35–2.63 | m | 4H | 2 piperazine CH$_2$s |
| 2.10–2.35 | m | 2H | CONHCH$_2$CH$_2$C$\underline{H}_2$N |
| 1.40–1.70 | m | 2H | CH$_2$C$\underline{H}_2$CH$_2$ |

EXAMPLE 12

3-(2-Chloro-6-fluorophenyl)-5-methyl-N-[3-[4-[2-(2,2,2-trifluoroethoxy)phenyl]1-piperazi-nyl]propyl]isoxazole-4-carboxamide a) 1-[2-(2,2,2,-Trifluoroethoxy)phenyl]-4-[3-(N-phthalimido)propyl]piperazine (Compound 12A)

The title compound was synthesised following the procedure described for Compound 1A of Example 1 but substituting 1-[2-(2,2,2-trifluoroethoxy)phenyl]piperazine for 1-(5-chloro-2-methoxyphenyl)piperazine. The reaction mixture was extracted with diethyl ether and the organic solution was dried over sodium sulphate and filtered on silica gel, washing the panel with diethyl ether. Evaporation to dryness in vacuo afforded the title product (91%). M.p. 111–113° C.

$^1$H-NMR (200 MHz) spectrum; Solvent: CDCl$_3$; Chemical shift (δ)

| | | | |
|---|---|---|---|
| 7.60–7.92 | m | 4H | phthalimide CHs |
| 6.80–7.10 | m | 4H | trifluoroethoxyphenyl CHs |
| 4.35 | q | 2H | OCH$_2$CF$_3$ |
| 3.80 | t | 2H | (CO)$_2$NC$\underline{H}_2$ |
| 2.75–3.12 | m | 4H | 2 piperazine CH$_2$s |
| 2.30–2.75 | m | 6H | (CO)$_2$NCH$_2$CH$_2$C$\underline{H}_2$N, 2 piperazine CH$_2$s |
| 1.75–2.10 | m | 2H | CH$_2$C$\underline{H}_2$CH$_2$ | b) 1-(3-Aminopropyl)-4-[2-(2,2,2,-trifluoroethoxy)phenyl]piperazine (Compound 12B)

The title compound was synthesised following the procedure described for Compound 1B of Example 1 but substituting Compound 12A for Compound 1A. Extraction of alkalinised filtrate with dichloromethane followed by purification by flash chromatograpy (chloroform:2N ammonia in methanol 10:1) afforded the title compound (78%) as an oil.

$^1$H-NMR (200 MHz) spectrum; Solvent: CDCl$_3$; Chemical shift (δ)

| | | | |
|---|---|---|---|
| 6.82–7.12 | m | 4H | aromatics CHs |
| 4.40 | q | 2H | OCH$_2$CF$_3$ |
| 2.95–3.25 | m | 4H | 2 piperazine CH$_2$s |
| 2.72–2.85 | m | 2H | H$_2$NC$\underline{H}_2$CH$_2$CH$_2$N |
| 2.52–2.72 | m | 4H | 2 piperazine CH$_2$s |
| 2.38–2.52 | m | 2H | H$_2$NCH$_2$CH$_2$C$\underline{H}_2$N |
| 1.55–1.80 | m | 4H | $\underline{H}_2$NCH$_2$C$\underline{H}_2$CH$_2$N | c) 3-(2-Chloro-6-fluorophenyl)-5-methyl-N-[3-[4-[2-(2,2,2-trifluoroethoxy)phenyl]-1-piperazi-nyl]propyl]isoxazole-4-carboxamide The title compound was synthesised according to the procedure described in Example 8 but using 3-(2-chloro-6-fluorophenyl)-5-methylisoxazole-4-carbonyl chloride instead of the crude 3-(4-fluorophenyl)isoxazole-4-carbonyl chloride and Compound 12B instead of Compound 8B. Washing the reaction mixture with 2 N sodium hydroxide, followed by the usual work-up and purification by flash chromatography (chloroform-2 N ammonia in methanol 100:3) afforded the title compound (92%) as an oil.

$^1$H-NMR (200 MHz) spectrum; Solvent: CDCl$_3$; Chemical shift (δ)

| | | | |
|---|---|---|---|
| 7.30–7.55 | m | 2H | chlorophenyl H3 and H5 |
| 7.10–7.23 | m | 1H | chlorophenyl H4 |
| 6.80–7.10 | m | 4H | trifluoroethoxyphenyl CHs |
| 5.60–6.30 | br | 1H | NH |
| 4.40 | q | 2H | OCH$_2$CF$_3$ |
| 3.25–3.50 | m | 2H | NHC$\underline{H}_2$ |
| 2.90–3.25 | m | 4H | 2 piperazine CH$_2$s |
| 2.78 | s | 3H | CH$_3$ |
| 2.10–2.75 | m | 6H | CONHCH$_2$CH$_2$C$\underline{H}_2$N, 2 piperazine CH$_2$s |
| 1.40–1.90 | m | 2H | CH$_2$C$\underline{H}_2$CH$_2$ |

EXAMPLE 13

3-(2-Chlorophenyl)-5-methyl-N-[3-[4-[2-(2,2,2-trifluoroethoxy)phenyl]-1-piperazinyl]propyl]-isoxazole-4-carboxamide The title compound was synthesised according to the procedure described in Example 8 but using 3-(2-chlorophenyl)-5-methylisoxazole-4-carbonyl chloride instead of the crude 3-(4-fluorophenyl)isoxazole-4-carbonyl chloride and Compound 12B instead of Compound 8B. Washing the reaction mixture with 2 N sodium hydroxide, followed by the usual work-up and purification by flash chromatography (chloroform-2 N ammonia in methanol 100:3) afforded the title compound (67.2%) as an oil.

$^1$H-NMR (200 MHz) spectrum; Solvent: CDCl$_3$; Chemical shift (δ)

| | | | |
|---|---|---|---|
| 7.35–7.62 | m | 4H | chlorophenyl CHs |
| 6.82–7.12 | m | 4H | trifluoroethoxyphenyl CHs |
| 5.50–5.80 | br | 1H | NH |
| 4.40 | q | 2H | OCH$_2$CF$_3$ |
| 3.22–3.42 | m | 2H | NHC$\underline{H}_2$ |
| 2.88–3.15 | m | 4H | 2 piperazine CH$_2$s |
| 2.78 | s | 3H | CH$_3$ |
| 2.35–2.63 | m | 4H | 2 piperazine CH$_2$s |
| 2.10–2.35 | m | 2H | CONHCH$_2$CH$_2$C$\underline{H}_2$N |
| 1.45–1.75 | m | 2H | CH$_2$C$\underline{H}_2$CH$_2$ |

EXAMPLE 14

3-(2,6-Dichlorophenyl)-5-methyl-N-[3-[4-[2-(2,2,2-trifluoroethoxy)phenyl]-1-piperazinyl]pro-pyl]isoxazole-4-carboxamide The title compound was synthesised according to the procedure described in Example 1 but using 3-(2,6-dichlorophenyl)-5-methylisoxazole-4-carboxylic acid instead of 3-phenyl-5-methyliso-xazole-4-carboxylic acid and Compound 12B instead of Compound 1B. Extraction with diethyl ether followed by purification by flash chromatography (chloroform-2 N ammonia in methanol 100:3) afforded the title compound (75%) as an oil.

$^1$H-NMR (200 MHz) spectrum; Solvent: CDCl$_3$; Chemical shift (δ)

| | | | |
|---|---|---|---|
| 7.35–7.60 | m | 3H | dichlorophenyl H3, H4 and H5 |
| 6.82–7.12 | m | 4H | trifluoroethoxyphenyl CHs |
| 5.40–5.75 | br | 1H | NH |
| 4.40 | q | 2H | OCH$_2$CF$_3$ |
| 3.22–3.42 | m | 2H | NHC$\underline{H}_2$ |
| 2.98–3.18 | m | 4H | 2 piperazine CH$_2$s |
| 2.80 | s | 3H | CH$_3$ |
| 2.40–2.65 | m | 4H | 2 piperazine CH$_2$s |
| 2.12–2.35 | m | 2H | CONHCH$_2$CH$_2$C$\underline{H}_2$N |
| 1.45–1.75 | m | 2H | CH$_2$C$\underline{H}_2$CH$_2$ |

EXAMPLE 15

N-[3-[4-[4-Fluoro-2-(2,2,2-trifluoroethoxy)phenyl]-1-piperazinyl]propyl]-3-phenyl isoxazole-4-carboxamide a) Methyl 3-phenyl-4-isoxazolecarboxylate (Compound 15A)

This compound was synthesised following the procedure described for Compound 8C but using benzaldoxime instead of 4-fluorobenzaldoxime as a starting material. The crude was purified twice by flash chromatography (toluene-acetone 96:4 followed by toluene) to give the title compound as an oil (35%).

$^1$H-NMR (200 MHz) spectrum; Solvent: CDCl$_3$; Chemical shift (δ)

| | | | |
|---|---|---|---|
| 9.01 | s | 1H | isoxazole H5 |
| 7.69–7.84 | m | 2H | phenyl CHs |
| 7.41–7.56 | m | 3H | phenyl CHs |
| 3.87 | s | 3H | COOCH$_3$ | b) 3-Phenyl-4-isoxazolecarboxylic acid (Compound 15B)

This compound was synthesised following the procedure described for Compound 8D but using Compound 15A instead of Compound 8C (90.2%). M.p. 162.7–164.5° C.

$^1$H-NMR (200 MHz) spectrum; Solvent: DMSO-d6; Chemical shift (δ)

| | | | |
|---|---|---|---|
| 13.07–13.23 | br | 1H | COOH |
| 9.65 | s | 1H | isoxazole H5 |
| 7.68–7.78 | m | 2H | phenyl CHs |
| 7.41–7.58 | m | 3H | phenyl CHs | c) N-[3-[4-[4-Fluoro-2-(2,2,2-trifluoroethoxy)phenyl]-1-piperazinyl]propyl]-3-phenyl isoxazole-4-carboxamide The title compound was synthesised following the method described in Example 8 but substituting Compound 15B for Compound 8D. The crude was purified by flash chromatography (ethyl acetate-2N ammonia in methanol 95:5) to give the title compound (88.4%). M.p. 95.8° C.

$^1$H-NMR (200 MHz) spectrum; Solvent: CDCl$_3$; Chemical shift ($\delta$)

| | | | |
|---|---|---|---|
| 9.09 | s | 1H | isoxazole H5 |
| 7.69–7.81 | m | 2H | phenyl CHs |
| 7.44–7.66 | m | 4H | phenyl CHs and NH |
| 6.84–6.95 | m | 1H | phenyl CH |
| 6.69–6.82 | m | 1H | phenyl CH |
| 6.58–6.67 | m | 1H | phenyl CH |
| 4.39 | q | 2H | OCH$_2$CF$_3$ |
| 3.51 | q | 2H | NHC$\underline{H}_2$ |
| 3.03–3.25 | m | 4H | 2 piperazine CH$_2$s |
| 2.79–2.97 | m | 4H | 2 piperazine CH$_2$s |
| 2.73 | t | 2H | CONHCH$_2$CH$_2$C$\underline{H}_2$N |
| 1.91 | q | 2H | CH$_2$C$\underline{H}_2$CH$_2$ |

EXAMPLE 16

3-(4-Fluorophenyl)-N-[3-[4-[2-(2,2,2-trifluoroethoxy)phenyl]-1-piperazinyl]propyl]isoxazole4-carboxamide The title compound was prepared according to the procedure described in Example 8, but substituting compound 12B for Compound 8B. Purification by flash chromatography (ethyl acetate-2 N ammonia in methanol 95:5) yielded the title product: 91.7%. M.p. 86.5–87.5° C.

$^1$H-NMR (200 MHz) spectrum; Solvent: CDCl$_3$; Chemical shift ($\delta$)

| | | | |
|---|---|---|---|
| 8.84 | s | 1H | isoxazole H5 |
| 7.31–7.40 | br | 1H | NH |
| 7.72–7.87 | m | 2H | trifluoroethoxyphenyl CHs |
| 7.10–7.27 | m | 2H | trifluoroethoxyphenyl CHs |
| 6.96–7.08 | m | 2H | fluorophenyl CHs |
| 6.81–6.94 | m | 2H | fluorophenyl CHs |
| 4.39 | q | 2H | OCH$_2$CF$_3$ |
| 3.50 | q | 2H | NHC$\underline{H}_2$ |
| 2.83–3.08 | m | 4H | 2 piperazine CH$_2$s |
| 2.53–2.64 | m | 4H | 2 piperazine CH$_2$s |
| 2.49 | t | 2H | CONHCH$_2$CH$_2$C$\underline{H}_2$N |
| 1.74 | q | 2H | CH$_2$C$\underline{H}_2$CH$_2$ |

EXAMPLE 17

3-Phenyl-N-[3-[4-[2-(2,2,2-trifluoroethoxy)phenyl]-1-piperazinyl]propyl]isoxazole-4-carboxamide The title compound was prepared according to the procedure described in Example 8, but substituting compound 15B for Compound 8D and Compound 12B for Compound 8B. Purification by flash chromatography (ethyl acetate-2 N ammonia in methanol 95:5) yielded the title product (88%). M.p. 94.5–95.6° C.

$^1$H-NMR (200 MHz) spectrum; Solvent: CDCl$_3$; Chemical shift ($\delta$)

| | | | |
|---|---|---|---|
| 8.87 | s | 1H | isoxazole H5 |
| 7.67–7.85 | m | 2H | phenyl CHs |
| 7.43–7.58 | m | 3H | phenyl CHs |
| 6.84–7.12 | m | 5H | NH and 4 trifluoroethoxyphenyl CHs |
| 4.39 | q | 2H | OCH$_2$CF$_3$ |
| 3.46 | q | 2H | NHCH$_2$ |
| 2.88–3.02 | m | 4H | 2 piperazine CH$_2$s |
| 2.47–2.59 | m | 4H | 2 piperazine CH$_2$s |
| 2.42 | t | 2H | CONHCH$_2$CH$_2$CH$_2$N |
| 1.81 | q | 2H | CH$_2$CH$_2$CH$_2$ |

EXAMPLE 18

3-(4-Fluorophenyl)-N-[3-[4-[4-fluoro-2-(2,2,2-trifluoroethoxy)phenyl]-1-piperazinyl]propyl]-5-methylisoxazole-4-carboxamide The title compound was prepared according to the procedure described in Example 1, but substituting Compound 8B for Compound 1B and 3-(4-fluorophenyl)-5-methylisoxazole-4-carboxylic acid (described in J.Chem.Soc. 1963, 5838–5845 but prepared following the method detailed in J.Am.Chem.Soc. 1985, 107,2721–2730) for 5-methyl-3-phenylisoxazole-4-carboxylic. Purification by flash chromatography (ethyl acetate -2 N ammonia in methanol 96:4) yielded the title product (77%). M.p. 150–151° C.

$^1$H-NMR (200 MHz) spectrum; Solvent: CDCl$_3$; Chemical shift ($\delta$)

| | | | |
|---|---|---|---|
| 7.60–7.65 | m | 2H | fluorophenyl CHs |
| 7.10–7.25 | m | 2H | fluorophenyl CHs |
| 6.70–6.90 | m | 2H | trifluoroethoxyphenyl H3, H6 |
| 6.55–6.65 | m | 1H | trifluoroethoxyphenyl H5 |
| 6.50 | bs | 1H | NH |
| 4.30–4.45 | m | 2H | OCH$_2$CF$_3$ |
| 3.45 | q | 2H | NHCH$_2$ |
| 2.75–2.95 | m | 4H | 2 piperazine CH$_2$s |
| 2.65 | s | 3H | CH$_3$ |
| 2.30–2.60 | m | 6H | 2 piperazine CH$_2$s and CONHCH$_2$CH$_2$CH$_2$N |
| 1.50–1.75 | m | 2H | CH$_2$CH$_2$CH$_2$ |

EXAMPLE 19

5-Ethyl-3-phenyl-N-[3-[4-[2-(2,2,2-trifluoroethoxy)phenyl]-1-piperazinyl]propyl]isoxazole-4-carboxamide a) N-(3-Chloropropyl)-5-ethyl-3-phenylisoxazole-4-carboxamide (Compound 19A)

A solution of 3.1 g of 5-ethyl-3-phenylisoxazole-4-carboxylic acid (prepared as described in J. Org. Chem. 1985, 50, 5660–5666), 2.94 g of 3-chloropropylamine hydrochloride, 2.62 mL of 92% diethyl cianoposphonate and 4.38 mL of triethylamine in 50 mL of anhydrous dimethylformamide was stirred at room temperature for 3 hours, poured into 500 mL of water and extracted with ethyl acetate (2×200 mL). The combined organic layers were washed with water, dried (sodium sulphate) and the solvent was evaporated under vacuum. The crude was purified by flash chromatography (ethyl acetate-petroleum ether 3:7) to give 3.35 g (73%) of the title compound. M.p. 75–76° C.

$^1$H-NMR (200 MHz) spectrum; Solvent: CDCl$_3$; Chemical shift (δ)

| 7.42–7.62 | m | 5H | phenyl CHs |
|---|---|---|---|
| 5.50 | bs | 1H | NH |
| 3.15 | q | 2H | CH$_2$CH$_3$ |
| 3.31–3.45 | m | 4H | CH$_2$CH$_2$CH$_2$Cl |
| 1.87 | tt | 2H | CH$_2$CH$_2$CH$_2$ |
| 1.38 | t | 3H | CH$_3$ | b) 5-Ethyl-3-phenyl-N-[3-[4-[2-(2,2,2-trifluoroethoxy)phenyl]-1-piperazinyl]propyl] isoxazole-4-carboxamide The title compound was obtained following the procedure described in Example 2 but substituting Compound 19A for Compound 2B and 1-[2-(2,2,2-trifluoroethoxy)phenyl] piperazine for 1-(2-hydroxy-5-chlorophenyl)piperazine. The crude was taken up with ethyl acetate and purified by flash chromatography eluting (ethyl acetate-2 N ammonia in methanol 98:2) to afford the title compound (54%). M.p. 102–104° C.

$^1$H-NMR (200 MHz) spectrum; Solvent: CDCl$_3$; Chemical shift (δ)

| 7.58–7.72 | m | 3H | phenyl CHs |
|---|---|---|---|
| 7.39–7.57 | m | 2H | phenyl CHs |
| 6.82–7.12 | m | 4H | trifluroethoxyphenyl CHs |
| 6.40 | bs | 1H | NH |
| 4.36 | q | 2H | CH$_2$CF$_3$ |
| 3.39 | dt | 2H | NHCH$_2$ |
| 3.10 | q | 2H | CH$_2$CH$_3$ |
| 2.71–3.01 | m | 4H | 2 piperazine CH$_2$s |
| 2.20–2.59 | m | 6H | 2 piperazine CH$_2$s and CONHCH$_2$CH$_2$CH$_2$N |
| 1.52–1.75 | m | 2H | CH$_2$CH$_2$CH$_2$ |
| 1.38 | t | 3H | CH$_3$ |

EXAMPLE 20

5-Ethyl-N-[3-[4-[4-fluoro-2-(2,2,2-trifluoroethoxy) phenyl]-1-piperazinyl]propyl]-3-phenylisoxazole-4-carboxamide The title compound was obtained following the procedure described in Example 2 but substituting Compound 19A for Compound 2B and 1-[4-fluoro-2-(2,2,2-trifluoroethoxy) phenyl]piperazine for 1-(2-hydroxy-5-chlorophenyl) piperazine. The crude was taken up with ethyl acetate and the crude was purified by flash chromatography (ethyl acetate-2 N ammonia in methanol 98:2) to afford the title compound (64%). M.p. 115–117° C.

$^1$H-NMR (200 MHz) spectrum; Solvent: CDCl$_3$; Chemical shift (δ)

| 7.58–7.72 | m | 3H | phenyl CHs |
|---|---|---|---|
| 7.39–7.55 | m | 2H | phenyl CHs |
| 6.68–6.88 | m | 2H | trifluroethoxyphenyl H3 and H6 |
| 6.60 | dd | 1H | trifluroethoxyphenyl H5 |
| 6.35 | bs | 1H | NH |

-continued

| 4.34 | q | 2H | CH$_2$CF$_3$ |
|---|---|---|---|
| 3.39 | dt | 2H | NHCH$_2$ |
| 3.10 | q | 2H | CH$_2$CH$_3$ |
| 2.68–3.01 | m | 4H | 2 piperazine CH$_2$s |
| 2.15–2.54 | m | 6H | 2 piperazine CH$_2$s and CONHCH$_2$CH$_2$CH$_2$N |
| 1.49–1.72 | m | 2H | CH$_2$CH$_2$CH$_2$ |
| 1.38 | t | 3H | CH$_3$ |

EXAMPLE 21

3-(4-Fluorophenyl)-5-methyl-N-[3-[4-[2-(2,2,2-trifluoroethoxy)phenyl]-1-piperazinyl]propyl] isoxazole-4-carboxamide The title compound was prepared according to the procedure described in Example 1, but substituting Compound 12B for Compound 1B and 3-(4-fluorophenyl)-5-methylisoxazole-4-carboxylic acid for 5-methyl-3-phenylisoxazole-4-carboxylic acid. Purification by flash chromatography (ethyl acetate-2 N ammonia in methanol 97:3) yielded the title product (66%). M.p.132–134° C.

$^1$H-NMR (200 MHz) spectrum; Solvent: CDCl$_3$; Chemical shift (δ)

| 7.60–7.65 | m | 2H | fluorophenyl CHs |
|---|---|---|---|
| 7.10–7.25 | m | 2H | fluorophenyl CHs |
| 6.85–7.05 | m | 4H | trifluoroethoxyphenyl CHs |
| 6.60 | bs | 1H | NH |
| 4.30–4.45 | m | 2H | OCH$_2$CF$_3$ |
| 3.45 | q | 2H | NHCH$_2$ |
| 2.85–3.00 | m | 4H | 2 piperazine CH$_2$s |
| 2.65 | s | 3H | CH$_3$ |
| 2.30–2.60 | m | 6H | 2 piperazine CH$_2$s and CONHCH$_2$CH$_2$CH$_2$N |
| 1.60–1.80 | m | 2H | CH$_2$CH$_2$CH$_2$ |

EXAMPLE 22

3-(2-Fluorophenyl)-N-[3-[4-[4-fluoro-2-(2,2,2-trifluoroethoxy)phenyl]-1-piperazinyl]propyl]-5-methylisoxazole-4-carboxamide The title compound was prepared according to the procedure described in Example 1, but substituting Compound 8B for Compound 1B and 3-(2-fluorophenyl)-5-methylisoxazole-4-carboxylic acid (described in J. Chem. Soc. 1963, 5838–5845 but prepared following the method detailed in J. Am. Chem. Soc. 1985, 107, 2721–2730) for 5-methyl-3-phenylisoxazole-4-carboxylic acid. Purification by flash chromatography (ethyl acetate-2 N ammonia in methanol 94:6) yielded the title product (83%). M.p. 110–112° C.

$^1$H-NMR (200 MHz) spectrum; Solvent: CDCl$_3$; Chemical shift (δ)

| 7.50–7.70 | m | 2H | fluorophenyl CHs |
|---|---|---|---|
| 7.15–7.35 | m | 2H | fluorophenyl CHs |
| 6.75–6.90 | m | 2H | trifluoroethoxyphenyl H3, H6 |
| 6.60–6.70 | m | 1H | trifluoroethoxyphenyl H5 |
| 6.20 | bs | 1H | NH |
| 4.40 | q | 2H | OCH$_2$CF$_3$ |
| 3.40 | q | 2H | NHCH$_2$ |
| 2.85–3.00 | m | 4H | 2 piperazine CH$_2$s |

-continued

| | | | |
|---|---|---|---|
| 2.70 | s | 3H | $CH_3$ |
| 2.30–2.60 | m | 6H | 2 piperazine $CH_2$s and $CONHCH_2CH_2CH_2N$ |
| 1.50–1.75 | m | 2H | $CH_2CH_2CH_2$ |

EXAMPLE 23

3-(2-Fluorophenyl)-5-methyl-N-[3-[4-[2-(2,2,2-trifluoroethoxy)phenyl]-1-piperazinyl]propyl]isoxazole-4-carboxamide The title compound was prepared according to the procedure described in Example 1, but substituting Compound 12B for Compound 1B and 3-(2-fluorophenyl)-5-methylisoxazole-4-carboxylic acid for 5-methyl-3-phenylisoxazole-4-carboxylic acid. Purification by flash chromatography (ethyl acetate-2 N ammonia in methanol 96:4) yielded the title product (61%). M.p. 127–128° C.

$^1$H-NMR (200 MHz) spectrum; Solvent: $CDCl_3$; Chemical shift (δ)

| | | | |
|---|---|---|---|
| 7.45–7.65 | m | 2H | fluorophenyl CHs |
| 7.15–7.35 | m | 2H | fluorophenyl CHs |
| 6.90–7.10 | m | 4H | trifluoroethoxyphenyl CHs |
| 6.30 | bs | 1H | NH |
| 4.40 | m | 2H | $OCH_2CF_3$ |
| 3.40 | q | 2H | $NHCH_2$ |
| 2.90–3.10 | m | 4H | 2 piperazine $CH_2$s |
| 2.70 | s | 3H | $CH_3$ |
| 2.30–2.60 | m | 6H | 2 piperazine $CH_2$s and $CONHCH_2CH_2CH_2N$ |
| 1.60–1.80 | m | 2H | $CH_2CH_2CH_2$ |

EXAMPLE 24

3-(3-Fluorophenyl)-N-[3-[4-[4-fluoro-2-(2,2,2-trifluoroethoxy)phenyl]-1-piperazinyl]propyl]-5-methylisoxazole-4-carboxamide The title compound was prepared according to the procedure described in Example 1, but substituting Compound 8B for Compound 1B and 3-(3-fluorophenyl)-5-methylisoxazole-4-carboxylic acid (described in J. Chem. Soc. 1963, 5845–5854 but prepared following the method detailed in J. Am. Chem. Soc. 1985, 107, 2721–2730) for 5-methyl-3-phenylisoxazole-4-carboxylic acid. Purification by flash chromatography (ethyl acetate-2 N ammonia in methanol 95:5) yielded the title product (93%). M.p. 86–91° C.

$^1$H-NMR (200 MHz) spectrum; Solvent: $CDCl_3$; Chemical shift (δ)

| | | | |
|---|---|---|---|
| 7.35–7.50 | m | 3H | fluorophenyl CHs |
| 7.15–7.30 | m | 1H | fluorophenyl CH |
| 6.70–6.90 | m | 2H | trifluoroethoxyphenyl H3, H6 |
| 6.55–6.70 | m | 1H | trifluoroethoxyphenyl H5 |
| 6.55 | bs | 1H | NH |
| 4.37 | q | 2H | $OCH_2CF_3$ |
| 3.45 | q | 2H | $NHCH_2$ |
| 2.70–2.95 | m | 4H | 2 piperazine $CH_2$s |
| 2.65 | s | 3H | $CH_3$ |
| 2.30–2.60 | m | 6H | 2 piperazine $CH_2$s and $CONHCH_2CH_2CH_2N$ |
| 1.50–1.75 | m | 2H | $CH_2CH_2CH_2$ |

EXAMPLE 25

3-(3-Fluorophenyl)-5-methyl-N-[3-[4-[2-(2,2,2-trifluoroethoxy)phenyl]-1-piperazinyl]propyl]isoxazole-4-carboxamide The title compound was prepared according to the procedure described in Example 1, but substituting Compound 12B for Compound 1B and 3-(3-fluorophenyl)-5-methylisoxazole-4-carboxylic acid for 5-methyl-3-phenylisoxazole-4-carboxylic acid. Purification by flash chromatography (ethyl acetate-2 N ammonia in methanol 96:4) yielded the title product (53%). M.p. 129–130° C.

$^1$H-NMR (200 MHz) spectrum; Solvent: $CDCl_3$; Chemical shift (δ)

| | | | |
|---|---|---|---|
| 7.35–750 | m | 3H | fluorophenyl CHs |
| 7.15–7.30 | m | 1H | fluorophenyl CH |
| 6.85–7.10 | m | 4H | trifluoroethoxyphenyl CHs |
| 6.60 | bs | 1H | NH |
| 4.40 | m | 2H | $OCH_2CF_3$ |
| 3.45 | q | 2H | $NHCH_2$ |
| 2.80–3.00 | m | 4H | 2 piperazine $CH_2$s |
| 2.70 | s | 3H | $CH_3$ |
| 2.30–2.60 | m | 6H | 2 piperazine $CH_2$s and $CONHCH_2CH_2CH_2N$ |
| 1.60–1.80 | m | 2H | $CH_2CH_2CH_2$ |

EXAMPLE 26

3-4(-Methoxyphenyl)-5-methyl-N-[3-[4-[2-(2,2,2-trifluoroethoxy)phenyl]-1-piperazinyl]propyl]isoxazole-4-carboxamide The title compound was prepared according tot he procedure described in Example 1, but substituting Compound 12B for Compound 1B and 3-(4-methoxyphenyl)-5-methylisoxazole-4-carboxylic acid (J. Chem Soc. 1963, 5838–5945) for 5-methyl-3-phenylisoxazole-4-carboxylic acid. Purification by flash chromatography (ethyl acetate-2 N ammonia in methanol 96:4) yielded the title product (60%). M.p. 130–135° C.

$^1$H-NMR (200 MHz) spectrum; Solvent: $CDCl_3$; Chemical shift (δ)

| | | | |
|---|---|---|---|
| 7.55 | dd | 2H | methoxyphenyl H2, 6 |
| 6.85–7.10 | m | 6H | trifluoroethoxyphenyl CHs and methoxyphenyl H3, 5 |
| 6.35 | t | 1H | NH |
| 4.35 | q | 2H | $OCH_2CF_3$ |
| 3.85 | s | 3H | $OCH_3$ |
| 3.40 | q | 2H | $NHCH_2$ |
| 2.80–3.00 | m | 4H | 2 piperazine $CH_2$s |
| 2.65 | s | 3H | $CH_3$ |
| 2.30–2.50 | m | 6H | 2 piperazine $CH_2^s$ and $CONHCH_2CH_2CH_2N$ |
| 1.55–1.75 | m | 2H | $CH_2CH_2CH_2$ |

EXAMPLE 27

N-[3-[4-[4-Fluoro-2-(2,2,2-trifluoroethoxy)phenyl]-1-piperazinyl]propyl]-3-(4-methoxyphenyl)-5-methylisoxazole-4-carboxamide The title compound was prepared according to the procedure described in Example 1, but substituting Compound 8B for Compound 1B and 3-(4-methoxyphenyl)-5-methylisoxazole-4-carboxylic for 5-methyl-3-phenylisoxazole-4-carboxylic acid. Purification by flash chromatography (ethyl acetate-2 N ammonia in methanol 95:5) yielded the title product (78%). M.p.106–109° C.

$^1$H-NMR (200 MHz) spectrum; Solvent: $CDCl_3$; Chemical shift ($\delta$)

| | | | |
|---|---|---|---|
| 7.55 | dd | 2H | methoxyphenyl H2, 6 |
| 7.00 | dd | 2H | methoxyphenyl H3, 5 |
| 6.55–6.90 | m | 3H | Trifluoroethoxyphenyl CHs |
| 6.35 | t | 1H | NH |
| 4.35 | q | 2H | $OCH_2CF_3$ |
| 3.85 | s | 3H | $OCH_3$ |
| 3.40 | q | 2H | $NHCH_2$ |
| 2.75–2.90 | m | 4H | 2 piperazine $CH_2$s |
| 2.65 | s | 3H | $CH_3$ |
| 2.30–2.50 | m | 6H | 2 piperazine $CH_2$s |
| 1.55–1.70 | m | 2H | $CH_2CH_2CH_2$ |

EXAMPLE 28

N-[3-[4-[4-Fluoro-2(2,2,2-trifluoroethoxy)phenyl]-1-piperazinyl]propyl]-3-phenyl-5-(2-phenylethyl)isoxazole-4-carboxamide a) 3-Phenyl-5-(2-phenylethyl)isoxazole-4-carboxylic acid (Compound 28A)

To a solution of 1.5 g of 5-methyl-3-phenyl-4-isoxazolecarboxylic acid in 50 mL of anhydrous tetrahydrofuran stirred at –78 ° C. under $N_2$ atmosphere, 5.9 mL of a 2.5M solution of n-buthyl lithium in n-hexane was added and the solution was stirred at –78° C. for 2 hours. Afterwards, 0.89 mL of benzyl bromide was added at –78° C. and the solution stirred at room temperature for 2 hours. After overnight resting, the solution was poured into water (300 mL), acidified with hydrochloric acid and extracted with ethyl acetate (2×200 mL). The combined organic layers were washed with water, dried (sodium sulphate) and the solvents were evaporated to dryness. The solid residue was washed with petroleum ether to give 1.82 g (84%) of the title compound as an amorphous solid.

$^1$H-NMR (200 MHz) spectrum; Solvent: $CDCl_3$; Chemical shift ($\delta$)

| | | | |
|---|---|---|---|
| 9.20–11.80 | br | 1H | COOH |
| 7.10–7.90 | m | 10H | PhCHs |
| 3.10 | t | 2H | $CH_2CH_2Ph$ |
| 3.45 | t | 2H | $CH_2CH_2Ph$ | b) N-[3-[4-[4-Fluoro-2-(2,2,2-trifluoroethoxy)phenyl]-1-piperazinyl-propyl]-3-phenyl-5-(2-phenylethyl)isoxazole-4-carboxamide The title compound was prepared according to the procedure described in Example 1, but substituting Compound 8B for Compound 1B and Compound 28A for 5-methyl-3-phenylisoxazole-4-carboxylic acid. Purification by flash chromatography (ethyl acetate-methanol 99:1) yielded the title product (32% as a yellow oil.

$^1$H-NMR (200 MHz) spectrum; Solvent: $CDCl_3$; Chemical shift ($\delta$)

| | | | |
|---|---|---|---|
| 7.58–7.71 | m | 2H | 3-phenyl H2 and H6 |
| 7.48–7.57 | m | 3H | 3-phenyl H3, H4 and H5 |
| 7.12–7.48 | m | 5H | phenylethyl CHs |
| 6.71–6.88 | m | 2H | fluorophenyl H3 and H6 |
| 6.60 | dd | 1H | fluorophenyl H5 |
| 6.00 | bt | 1H | NH |
| 4.38 | q | 2H | $CH_2CF_3$ |
| 3.22–3.41 | m | 4H | $CONHCH_2CH_2CH_2N$ and $CH_2CH_2Ph$ |
| 3.08 | t | 2H | $CH_2CH_2Ph$ |
| 2.68–2.91 | m | 4H | 2 piperazine $CH_2$s |
| 2.35–2.51 | m | 4H | 2 piperazine $CH_2$s |
| 2.25 | t | 1H | $CONHCH_2CH_2CH_2N$ |
| 1.55 | tt | 2H | $CONHCH_2CH_2CH_2N$ |

EXAMPLE 29

N-[3-[4-[4-Fluoro-2-(2,2,2-trifluoroethoxy)phenyl]-1-piperazinyl]propyl]-3-phenyl-5-(3-phenylpropyl)isoxazole-4-carboxamide a) 3-Phenyl-5-(3-phenylpropyl)isoxazole-4-carboxylic acid (Compound 29A)

The title compound was prepared as described for Compound 28A but substituting 2-phenylethylbromide for benzyl bromide. The crude was purified by flash chromatography (ethyl acetate-petroleum ether-acetic acid 1:1:0.01 mL) to afford the title compound (72%).

$^1$H-NMR (200 MHz) spectrum; Solvent: $CDCl_3$; Chemical shift ($\delta$)

| | | | |
|---|---|---|---|
| 9.20–11.80 | br | 1H | COOH |
| 7.61–7.75 | m | 3H | phenyl H3, H4 and H5 |
| 7 45–7.75 | m | 2H | phenyl H2 and H6 |
| 7.10–7.35 | m | 5H | $CH_2CH_2CH_2Ph$ |
| 3.20 | t | 2H | $CH_2CH_2CH_2Ph$ |
| 2.75 | t | 2H | $CH_2CH_2CH_2Ph$ |
| 2.15 | tt | 2H | $CH_2CH_2CH_2Ph$ | b) N-[3-[4-[4-Fluoro-2-(2,2,2-trifluoroethoxy)phenyl]-1-piperazinyl-propyl]-3-phenyl-5-(3-phenylpropyl)isoxazole-4-carboxamide The title compound was prepared according to the procedure described in Example 1, but substituting Compound 8B for Compound 1B and Compound 29A for 5-methyl-3-phenylisoxazole-4-carboxylic acid. Purification by flash chromatography (ethyl acetate-petroleum ether 99:1) yielded the title product (42%) as a yellow oil.

$^1$H-NMR (200 MHz) spectrum; Solvent: $CDCl_3$; Chemical shift ($\delta$)

| | | | |
|---|---|---|---|
| 7.60–7.75 | m | 2H | isoxazole 3-phenyl H2 and H6 |
| 7.48–7.57 | m | 3H | isoxazole 3-phenyl H3, H4 and H5 |
| 7.12–7.40 | m | 5H | $CH_2CH_2CH_2Ph$ |
| 6.71–6.88 | m | 2H | fluorophenyl H3 and H6 |
| 6.62 | dd | 1H | fluorophenyl H5 |
| 6.40 | bt | 1H | NH |
| 4.38 | q | 2H | $CH_2CF_3$ |
| 3.48 | dt | 2H | $CONHCH_2CH_2CH_2N$ |
| 3.12 | t | 2H | $CH_2CH_2CH_2Ph$ |
| 2.76–2.91 | m | 4H | 2 piperazine $CH_2$s |
| 2.75 | t | 2H | $CH_2CH_2CH_2Ph$ |
| 2.35–2.51 | m | 4H | 2 piperazine $CH_2$s |

| | | | |
|---|---|---|---|
| 2.25 | t | 2H | CONHCH$_2$CH$_2$CH$_2$N |
| 2.14 | tt | 2H | CH$_2$CH$_2$CH$_2$Ph |
| 1.55 | tt | 2H | CONHCH$_2$CH$_2$CH$_2$N |

EXAMPLE 30

N-[3-[4-[4-Fluoro-2-methoxyphenyl]-1-piperazinyl]propyl]-5-methyl-3-phenylisoxazole-4-carboxamide The title compound was prepared following the procedure described in Example 2c but substituting compound 2A with 1-(4-fluoro-2-methoxyphenyl)piperazine (U.S. Pat. No. 5,358,948) and heating at 190° C. for 40 min. The crude was purified by flash chromatography (ethyl acetate-2N methanolic ammonia 96:4) to afford the title compound (79%). M.p. 162–163° C.

$^1$H-NMR (200 MHz) spectrum; Solvent: CDCl$_3$; Chemical shift (δ)

| | | | |
|---|---|---|---|
| 7.60–7.70 | m | 2H | phenyl H 2,6 |
| 7.45–7.55 | m | 3H | phenyl H3,4,5 |
| 6.55–6.70 and 6.73–6.85 | 2m | 3H | methoxyphenyl H3,5,6 |
| 6.35 | bs | 1H | NH |
| 3.90 | s | 3H | OCH$_3$ |
| 3.37 | q | 2H | CONHC<u>H</u>$_2$CH$_2$CH$_2$ |
| 2.75–2.90 | m | 4H | 2 piperazine CH$_2$s |
| 2.70 | s | 3H | CH3 |
| 2.40–2.55 | m | 4H | 2 piperazine CH$_2$s |
| 2.30 | t | 2H | CONHCH$_2$CH$_2$C<u>H</u>$_2$ |
| 1.55–1.70 | m | 2H | CH$_2$CH$_2$C<u>H</u>$_2$ |

EXAMPLE 31

N-[3-[4-(4-Fluoro-2-methylphenyl)-1-piperazinyl]propyl]-5-methyl-3-phenylisoxazole-4-carboxamide a) 1-(4-Fluoro-2-methylphenyl)piperazine (Compound 31A)

The title compound was prepared following the method described for the Compound 5C of Example 5 but starting from 4-fluoro-2-methylaniline instead of compound 5B and using a 10:1 mixture of 1,2-dichlorobenzene and n-hexanol at 185° C. as solvent. Purification by flash chromatography (chloroform-2N ammonia in methanol 100:3 to 100:5) afforded the title compound (70%) as a light brown solid.

$^1$H-NMR (200 MHz) spectrum; Solvent: CDCl$_3$; Chemical shift (δ)

| | | | |
|---|---|---|---|
| 6.87–7.05 | m | 3H | phenyl CHs |
| 3.00–3.15 | m | 4H | 2 piperazine CH$_2$s |
| 2.85–2.95 | m | 5H | 2 piperazine CH$_2$s and NH |
| 2.30 | s | 3H | CH$_3$ | b) N-[3-[4-(4-Fluoro-2-methylphenyl)-1-piperazinyl]-5-methyl-3-phenylisoxazole-4-carboxamide A stirred mixture of 0.380 g of Compound 31A, 0.50 mL of N,N-diisopropylethylamine, 0.545 g of Compound 2B and 3 mL of N,N-dimethylformamide was heated at 120° C. for 5 h. The solution was diluted with water (60 mL) and extracted with dichloromethane (3×30 mL); the organic layer was washed with water (3×20 mL), dried (anhydrous sodium sulphate) and evaporated to dryness in vacuo. The residue was purified by flash chromatography (chloroform-2N methanolic ammonia 100:1) affording 0.373 g (43.7%) of the title compound as an ivory solid. M.p. 139–141° C.

$^1$H-NMR (200 MHz) spectrum; Solvent: CDCl$_3$; Chemical shift (δ)

| | | | |
|---|---|---|---|
| 7.58–7.73 | m | 2H | phenyl H2,6 |
| 7.42–7.58 | m | 3H | phenyl H3,4,5 |
| 6.77–6.97 | m | 3H | fluorophenyl CHs |
| 6.35 | bs | 1H | CONH |
| 3.30–3.50 | m | 2H | CONHC<u>H</u>$_2$CH$_2$CH$_2$ |
| 2.58–2.75 | m | 7H | piperazine CH$_{2}$s, isoxazole CH$_3$ |
| 2.18–2.50 | m | 9H | CONHCH$_2$CH$_2$C<u>H</u>$_2$, phenyl CH$_3$, 2 piperazine CH$_2$s |
| 1.50–1.72 | m | 2H | CONHCH$_2$C<u>H</u>$_2$CH$_2$ |

EXAMPLE 32

N-[3-[4-(4-Chloro-2-methylphenyl)-1-piperazinyl]propyl]-5-methyl-3-phenylisoxazole-4-carboxamide a) 1-(4-Chloro-2-methylphenyl)piperazine (Compound 32A)

The title compound was prepared following the method described for the Compound 31A of Example 31 but starting from 4-chloro-2-methylaniline instead of 4-fluoro-2-methylaniline. Purification by flash chromatography (chloroform-2N ammonia in methanol 100:3 to 100:5) afforded the title compound (73%) as an oil.

$^1$H-NMR (200 MHz) spectrum; Solvent: CDCl$_3$; Chemical shift (δ)

| | | | |
|---|---|---|---|
| 7.05–7.20 | m | 2H | phenyl H3,5 |
| 6.95 | d | 1H | phenyl H6 |
| 2.95–3.05 | m | 4H | 2 piperazine CH$_2$s |
| 2.75–3.85 | m | 4H | 2 piperazine CH$_2$s |
| 2.28 | s | 3H | CH$_3$ |
| 1.70 | s | 1H | NH | b) N-[3-[4-(4-Chloro-2-methylphenyl)-1-piperazinyl]propyl]-5-methyl-3-phenylisoxazole-4-carboxamide The title compound was prepared following the method described for Example 31, but using Compound 32A instead of compound 31A. The residue was purified by flash chromatography (chloroform-2N methanolic ammonia 100:1) affording the title compound (47% as an ivory solid. M.p. 147–150° C.

$^1$H-NMR (200 MHz) spectrum; Solvent: CDCl$_3$; Chemical shift (δ)

| | | | |
|---|---|---|---|
| 7.58–7.75 | m | 2H | phenyl H2,6 |
| 7.40–7.58 | m | 3H | phenyl H3,4,5 |
| 7.07–7.20 | m | 2H | chlorophenyl H3 and H5 |
| 6.85 | d | 1H | chlorophenyl H6 |
| 6.32 | bs | 1H | CONH |

-continued

| | | | |
|---|---|---|---|
| 3.30–3.50 | m | 2H | CONHC$\underline{H}_2$CH$_2$CH$_2$ |
| 2.62–2.80 | m | 7H | 2 piperazine CH$_2$s isoxazole CH$_3$ |
| 2.18–2.52 | m | 9H | CONHCH$_2$CH$_2$C$\underline{H}_2$, phenyl CH$_3$, 2 piperazine CH$_2$s |
| 1.52–1.75 | m | 2H | CONHCH$_2$C$\underline{H}_2$CH$_2$ |

EXAMPLE 33

N-[3-[4-[4-Fluoro-2-(1-methylethoxy)phenyl]-1-piperazinyl]propyl]-5-methyl-3-phenylisoxazole-4-carboxamide The title compound was prepared following the procedure described in Example 2c but substituting Compound 2A with 1-[4-fluoro-2-(1-methylethoxy)phenyl]piperazine (U.S. Pat. No. 5,569,659) and heating at 190° C. for 40 min. The crude was purified by flash chromatography (dichloromethane-2N methanolic ammonia 95:5) to afford the title compound (55%) as an ivory solid.

$^1$H-NMR (200 MHz) spectrum; Solvent: CDCl$_3$; Chemical shift ($\delta$))

| | | | |
|---|---|---|---|
| 7.60–7.70 | m | 2H | phenyl H2,6 |
| 7.45–7.55 | m | 3H | phenyl H3,4,5 |
| 6.70–6.80 and 6.55–6.65 | 2m | 3H | isopropoxyphenyl H3,5,6 |
| 6.35 | br | 1H | NH |
| 4.55 | q | 1H | CH |
| 3.40 | q | 2H | CONHC$\underline{H}_2$CH$_2$CH$_2$ |
| 2.75–2.95 | m | 4H | 2 piperazine CH$_2$s |
| 2.70 | s | 3H | CH$_3$ |
| 2.35–2.50 | m | 4H | 2 piperazine CH$_2$s |
| 2.30 | t | 2H | CONHCH$_2$CH$_2$C$\underline{H}_2$ |
| 1.55–1.70 | m | 2H | CH$_2$C$\underline{H}_2$CH$_2$ |
| 1.35 | d | 6H | (CH$_3$)$_2$ |

EXAMPLE 34

N-[3-[4-(4-Chloro-2-methoxyphenyl)-1-piperazinyl]propyl]-5-methyl-3-phenylisoxazole-4-carboxamide The title compound was prepared following the method described in Example 31, but using 1-(4-chloro-2-methoxyphenyl)piperazine (prepared as described in U.S. Pat. No. 5,859,014) instead of compound 31A. The residue was purified by flash chromatography (chloroform-2 N methanolic ammonia 100:0.7) affording the title compound (47%) as an ivory solid. M.p. 145–146° C.

$^1$H-NMR (200 MHz) spectrum; Solvent: CDCl$_3$; Chemical shift ($\delta$)

| | | | |
|---|---|---|---|
| 7.58–7.72 | m | 2H | phenyl H2, H6 |
| 7.40–7.58 | m | 3H | phenyl H3, H4, H5 |
| 6.68–7.10 | m | 3H | chlorophenyl Chs |
| 6.31 | bs | 1H | CONH |
| 3.82 | s | 3H | OCH$_3$ |
| 3.28–3.50 | m | 2H | CONHC$\underline{H}_2$CH$_2$CH$_2$ |
| 2.74–2.98 | m | 4H | 2 piperazine CH$_2$s |
| 2.68 | s | 3H | CH$_3$ |
| 2.38–2.55 | m | 4H | 2 piperazine CH$_2$s |
| 2.21–2.38 | m | 2H | CONHCH$_2$CH$_2$C$\underline{H}_2$ |
| 1.50–1.72 | m | 2H | CONHCH$_2$C$\underline{H}_2$CH$_2$ |

EXAMPLE 35

N-[3-[4-[4-Chloro-2-(2-methylethoxy)phenyl]-1-piperazinyl]propyl]-5-methyl-3-phenylisoxa-zole-4-carboxamide a) 4-Chloro-2-isopropoxynitrobenzene (Compound 35A)

To a stirred suspension of 4-chloro-2-nitrophenol (2.9 g) and potassium carbonate (2.5 g) in N,N-dimethylformamide (30 mL) was added 2-bromopropane (1.75 mL). The mixture was heated at 75–80° C. for 6 h. After cooling to room temperature, the suspension was poured into water (600 mL) and extracted with diethyl ether (3×100 mL); the combined organic layers were dried over anhydrous sodium sulphate and evaporated to dryness to give 3.5 g (97%) of the title compound as a yellow oil, used in the next step without further purification.

$^1$H-NMR (200 MHz) spectrum; Solvent: CDCl$_3$; Chemical shift ($\delta$)

| | | | |
|---|---|---|---|
| 7.75 | d | 1H | H6 |
| 7.08 | d | 1H | H3 |
| 6.91–7.01 | dd | 1H | H5 |
| 4.58–4.75 | m | 1H | C$\underline{H}$(CH$_3$)$_2$ |
| 1.41 | d | 6H | CH(C$\underline{H}_3$)$_2$ | b) 4-Chloro-2-isopropoxyaniline (Compound 35B)

To a solution of Compound 35A (1 g) in methanol (30 mL) was added Raney-Ni (0.05 g) and the resulting mixture was cooled at 0–5° C.; 98% hydrazine hydrate (1.5 mL) was dropped in at the same temperature and the suspension stirred at room temperature for 2 h. The catalyst was filtered off and the solvents evaporated in vacuo. The crude was dissolved in dichloromethane (100 mL) and washed with water (60 mL); the organic layer was dried over sodium sulphate and evaporated to dryness affording 0.78 g (90%) of the title product as a yellow oil.

$^1$H-NMR (200 MHz) spectrum; Solvent: CDCl$_3$; Chemical shift ($\delta$)

| | | | |
|---|---|---|---|
| 6.72–6.81 | m | 2H | phenyl Chs |
| 6.61–6.69 | m | 1H | phenyl CH |
| 4.41–4.59 | m | 1H | C$\underline{H}$(CH$_3$)2 |
| 3.65–3.96 | br | 2H | NH2 |
| 1.46 | d | 6H | CH(C$\underline{H}_3$)$_2$ | c) 1-(4-Chloro-2-isopropoxyphenyl)piperazine (Compound 35C)

The title compound was prepared following the procedure described for compound 5C but substituting Compound 35B for Compound 5B and heating at 185° C. for 5 h. Extraction with dichloromethane followed by the usual work-up procedure afforded a crude which was purified by flash chromatography (CHCl$_3$-2 N methanolic ammonia 97:3) to afford the title compound as a brown oil (68%).

$^1$H-NMR (200 MHz) spectrum; Solvent: CDCl$_3$; Chemical shift ($\delta$)

| | | | |
|---|---|---|---|
| 6.81–6.93 | m | 3H | phenyl CHs |
| 4.49–4.65 | m | 1H | —C$\underline{H}$(CH$_3$)$_2$ |
| 2.91–3.11 | m | 8H | piperazine CH2s |
| 1.65–1.79 | br | 1H | NH |
| 1.38 | d | 6H | —CH(C$\underline{H}_3$)$_2$ | d) N-[3-[4-[4-Chloro-2-(2-methylethoxy)phenyl]-1-piperazinyl]propyl]-5-methyl-3-phenylisoxazo-le-4-carboxamide The title compound was prepared following the method described in Example 31, but using Compound 35C instead of Compound 31A and heating at 200° C. for 20 min. The residue was purified by flash chromatography (dichloromethane-2 N methanolic ammonia 95:5) affording the title compound (63%) as an grey powder. M.p. 116–120° C.

$^1$H-NMR (200 MHz) spectrum; Solvent: CDCl$_3$; Chemical shift (δ)

| | | | |
|---|---|---|---|
| 7.58–7.75 | m | 2H | phenyl CHs |
| 7.41–7.56 | m | 3H | phenyl CHs |
| 6.81–6.95 | m | 2H | chlorophenyl Chs |
| 6.68–6.79 | m | 1H | chlorophenyl CH |
| 6.28–6.41 | br | 1H | CONH |
| 4.45–4.66 | m | 1H | C$\underline{H}$(CH$_3$)2; |
| 3.30–3.45 | m | 2H | CONHC$\underline{H}_2$CH$_2$CH$_2$N |
| 2.78–2.95 | m | 4H | 2 piperazine CH2s |
| 2.68 | s | 3H | isoxazole CH$_3$ |
| 2.31–2.49 | m | 4H | 2 piperazine CH$_2$s |
| 2.19–2.29 | m | 2H | CONHCH$_2$C$\underline{H}_2$CH$_2$N |
| 1–52–1.74 | m | 2H | CONHC$\underline{H}_2$CH$_2$CH$_2$N |
| 1.34 | d | 6H | CH(C$\underline{H}_3$)$_2$ |

EXAMPLE 36

N-[3-[4-(2-Ethoxy-4-fluoro)-1-piperazinyl]propyl]-5-methyl-3-phenylisoxazole-4-carboxamide The title compound was prepared following the method described in Example 31, but using 1-(2-ethoxy-4-fluorophenyl)piperazine (prepared as described in U.S. Pat. No. 6,046,329) instead of compound 31A. The residue was purified by flash chromatography (chloroform-2 N methanolic ammonia 100:1) affording the title compound (61%) as a brown solid. M.p. 130–132° C.

$^1$H-NMR (200 MHz) spectrum; Solvent: CDCl$_3$; Chemical shift (δ)

| | | | |
|---|---|---|---|
| 7.58–7.72 | m | 2H | phenyl H 2, H6 |
| 7.40–7.58 | m | 3H | phenyl H 3, H4, H5 |
| 6.70–6.85 | m | 1H | fluorophenyl CH |
| 6.50–6.65 | m | 2H | fluorophenyl Chs |
| 6.36 | bs | 1H | CONH |
| 4.05 | q | 2H | OCH2CH3 |
| 3.30–3.50 | m | 2H | CONHC$\underline{H}_2$CH$_2$CH$_2$ |
| 2.75–2.92 | m | 4H | piperazine CH2s |
| 2 2.68 | s | 3H | isoxazole CH3 |
| 2.38–2.52 | m | 4H | 2 piperazine CH2s |
| 2.31 | t | 2H | CONHCH$_2$CH$_2$CH$_2$ |
| 1.52–1.72 | m | 2H | CONHCH$_2$C$\underline{H}_2$CH$_2$ |
| 1.45 | t | 3H | OCH$_2$CH$_3$ |

EXAMPLE 37

Determination of Affinity for Cloned $\alpha_1$ Adrenergic Receptors and 5-HT$_{1A}$ Serotoninergic Receptors by Radioligand Binding Assay Determination of affinity for cloned subtypes of the $\alpha_1$-adrenoceptor was performed in membranes from cells transfected by electroporation with DNA expressing the genes encoding each $\alpha_1$-adrenoceptor subtype.

Cloning and stable expression of the $\alpha_1$-adrenoceptor gene were performed as previously described (Testa et al., Pharmacol. Comm., 6:79–86, 1995 and references). The cell membranes were incubated in 50 nM Tris, pH 7.4, with 0.2 nM [$^3$H]prazosin, in a final volume of 1.02 mL for 30 minutes at 25° C., in the absence or presence of competing drugs (1 pM-10 μM). Non-specific binding was determined in the presence of 10 μM phentolamine. Incubation was stopped by addition of ice-cold Tris buffer and rapid filtration through 0.2%-polyethyleneimine pretreated Schleicher & Schuell GF52 filters.

Genomic clone G-21 coding for the human 5-HT$_{1A}$-serotoninergic receptor was stably transfected in a human cell line (HeLa) (Fargin et al., J. Biol. Chem., 284:14848–14852, 1989). HeLa cells were grown as monolayers in Dulbecco's modified Eagle's medium (DMEM), supplemented with 10% foetal calf serum and gentamicin (100 μg/mL), 5% CO$_2$ at 37° C. The cells were detached from the growth flask at 95% confluence by a cell scraper and were lysed in ice-cold Tris-5-mM and EDTA-5-mM buffer (pH 7.4). The homogenates were centrifuged at 40000×g×20 minutes and the membranes were resuspended in a small volume of ice-cold buffer containing Tris 5 mM and EDTA 5 mM (pH 7.4) and immediately frozen and stored at −70° C. until use.

On the day of experiment, the cell membranes were resuspended in a buffer containing 50 mM Tris (pH 7.4), 2.5 mM MgCl$_2$, 10 μM pargyline (Fargin et al., Nature, 335:358–360, 1988). The membranes were incubated in a final volume of 1 mL for 30 minutes at 30° C. with 1.2 nM [$^3$H]8-OH-DPAT, in the absence or presence of test molecules. Non-specific binding was determined in the presence of 10 μM 5-HT. Incubation was stopped by addition of ice-cold Tris buffer and rapid filtration through 0.2%-polyethyleneimine pretreated Schleicher & Schuell GF52 filters.

Inhibition of specific binding of the radioligands by the test drugs was analysed to estimate the IC$_{50}$ value by using the non-linear curve-fitting program Allfit (De Lean et al., Am. J. Physiol., 235:E97-E102, 1978).

The IC$_{50}$ value was converted to an affinity constant (Ki) by the equation of Cheng et al. (Biochem. Pharmacol., 22:3099–3108, 1973). Data were expressed as mean Ki.

Results

The compounds of the invention exhibited the desired potency and selectivity at $\alpha_1$ adrenoceptors, as shown in Table 1.

TABLE 1

Affinity of the different compounds tested for recombinant $\alpha_1$-adrenoceptor subtypes and 5-HT$_{1A}$ receptor.

| | Receptors (Ki, nM) | | | |
|---|---|---|---|---|
| Example | $\alpha_{1a}$ | $\alpha_{1b}$ | $\alpha_{1d}$ | 5-HT$_{1A}$ |
| 1 | 0.77 | 23.64 | 2.72 | 435.66 |
| 2 | 1.16 | 9.97 | 25.16 | 49.46 |
| 3 | 0.066 | 36.21 | 1.45 | 11.72 |
| 4 | 16.99 | 569.79 | 128.43 | >1000 |
| 5 | 0.05 | 11.52 | 0.33 | 191.74 |
| 6 | 0.35 | 69.5 | 18.89 | 316.9 |

TABLE 1-continued

Affinity of the different compounds tested for recombinant α₁-adrenoceptor subtypes and 5-HT$_{1A}$ receptor.

| Example | Receptors (Ki, nM) | | | |
|---|---|---|---|---|
| | $\alpha_{1a}$ | $\alpha_{1b}$ | $\alpha_{1d}$ | 5-HT$_{1A}$ |
| 7 | 0.918 | 7.49 | 38.93 | 1000 |
| 8 | 0.11 | 28.08 | 25/81 | 201.9 |
| 9 | 0.4 | 24.1 | 6.15 | 341.9 |
| 10 | 2.28 | 24.23 | 38.58 | 169.55 |
| 11 | 0.12 | 31.15 | 4.66 | 242.11 |
| 12 | 0.16 | 21.38 | 2.19 | 29.98 |
| Compound A | 0.65 | 3.87 | 1.51 | 4.53 |
| Prazosin | 0.54 | 0.42 | 0.23 | >10000 |

EXAMPLE 38

In vitro Evaluation of Functional Antagonism for $\alpha_{1L}$ Adrenoceptors

The functional α₁-antagonistic activity of the test compounds against noradrenaline(NA)-induced contractions of rabbit aorta pretreated with chloroethylclonidine ($\alpha_{1L}$ receptor) was evaluated according to the method of Testa et al. (J. Pharmacol. Exp. Ther., 281:1284–1293, 1997). Adult male New Zealand rabbits were sacrificed by cervical dislocation. The aorta was removed, placed in Krebs-Henseleit buffer and dissected free of adhering tissue. Rings were prepared from each artery (8 rings per aorta, about 4–5 mm wide) and suspended in 20 mL organ bath containing Krebs bicarbonate buffer of the following composition (mM): NaCl 112.0, KCl 5.0, CaCl₂ 2.5, KH₂PO₄ 1.0, MgSO₄ 1.2, NaHCO₃ 12.0 and glucose 11.1, and equilibrated at 37° C. with 95% O2:5% CO₂. Desmethylimipramine (0.1 μM) and corticosterone (1 μM) to block neuronal and extraneuronal uptake of NA, (±)-propranol (1 μM) to block β adrenoceptors and yohimbine (0.1 μM) to block α₂ adrenoceptors were added to the buffer. The tissues were subject to a passive load of 2 g and the developed tension was measured using isometric transducers (Basile 7003).

The preparations were allowed to equilibrate for 60 minutes and then primed every 30 minutes with 10 μM NA for three times. The aortic rings were then incubated with the alkylating agent chloroethyldlonidine (5×10⁻⁵M) for 30 minutes and then washed extensively three times (in 0.5 hours) before constructing the NA-concentration/response curve. After washout of NA and re-equilibration of the tissue (45 min), the drug to be tested was added and, after 30 minutes, a second cumulative-NA-concentration/response curve constructed. Each antagonist concentration was tested using 2–3 aortic rings from different rabbits.

Dose ratios (i. e., the ratio between the concentrations of noradrenaline required to produce half-maximal response in the presence and in the absence of the test antagonist) were calculated at each concentration of the compounds. The logarithm of these dose ratio −1 was plotted against the logarithm of the compound concentrations (Schild plot) to evaluate the affinity constant Kb.

When only one or two concentrations of the test compounds were utilised, the apparent Kb value was calculated using the formula: Kb=[B]/(DOSE RATIO−1), where B is the antagonist concentration.

Results

The compounds tested showed good affinity for the $\alpha_{1L}$ adrenoceptor subtype. The data are expressed as pKb in Table 2.

TABLE 2

Functional affinity of the tested compounds for the $\alpha_{1L}$ adrenoceptor subtype.

| Example | pKb |
|---|---|
| 3 | 8.47 |
| 5 | 8.79 |
| Compound A | 8.91 |
| Prazosin | 7.68 |

EXAMPLE 39

Effects on Urethral Contractions (Induced by Noradrenaline Injection and Hypogastric-nerve Stimulation) and on Blood Pressure in Dogs After Intravenous Administration The experiments were performed according to the method of Imagawa et al. (J. Pharmacol. Methods, 22:103–111, 1989) with substantial modifications, as follows: adult male beagle dogs, weighing 8–10 kg, were anaesthetised with pentobarbital sodium (30 mg/kg i.v. and 2 mg/kg/h i.v.), intubated and spontaneously ventilated with room air. In order to monitor systemic blood pressure (BP), a polyethylene (PE) catheter was introduced into the aortic arch through the left femoral artery. A collateral of the left femoral vein was cannulated for infusion of anaesthetic, and the right femoral vein was cannulated for administration of the compounds. For intraarterial (i.a.) injection of noradrenaline (NA), a PE catheter was introduced into the lower portion of the abdominal aorta via the right external iliac artery. Through such procedure, NA was selectively distributed to the lower urinary tract. A paramedian vertical suprapubic incision extending from the base of the pelvis to the mid-abdominal region was made and the bladder and the prostate were exposed. The bladder was manually emptied with a syringe. The hypogastric nerve was freed from surrounding tissue and cut 1 cm distal from the inferior mesenteric ganglion. The distal end of the right or left branch of the nerve was placed on a bipolar platinum electrode. Prostatic urethral pressure was monitored with a Mikro-tip catheter (5F) introduced into the bladder via the external urethral meatus, and withdrawn until the pressure transducer was positioned in the prostatic region of the urethra. A ligature was secured between the neck of the bladder and urethra to isolate the response of the latter and to avoid any interaction with the bladder. Another ligature was put around the Mikro-tip catheter at the external meatus, to secure the catheter itself. The hypogastric nerve stimulation was made with a train of rectangular pulses of 10–15 V, 10–30 Hz, width 5 msec, 8 sec duration.

After a stabilizing period following the surgical procedure (30 minutes), in which arterial and prostatic urethral pressure were continuously monitored as basal values, i.a. administration of NA and stimulation of the hypogastric nerve were alternately made at intervals of 10 minutes.

The dose of NA and the parameter of hypogastric nerve stimulation chosen were such as to produce an increase of at least 100% in urethral pressure. The test compounds were administered intravenously in a cumulative manner with intervals of 15–20 min between administrations. Both i.a. injections of NA and stimulations of the hypogastric nerve were repeated 5 minutes after every dosing of test compound with intervals of about 5 minutes between two stimulations. In order to compare the effects of the administered compound, dose/response curves were constructed by computing, at the peak effect, the percent decrease in diastolic blood pressure and the percent inhibition of the increase in urethral pressure induced by both types of stimulation used. Linear regression equations were then used in order to evaluate the theoretical effectiveness as $ED_{25}$ (the effective dose inducing a 25% decrease in diastolic blood pressure) and $ID_{50}$ (the dose inhibiting by 50% the increase in urethral pressure).

Results

The effects obtained after intravenous administration of the compounds of Examples 1, 3 and 5 are shown in Table 3. The effects obtained after injection of prazosin and Rec 15/2739 are also shown in Table 3.

TABLE 3

Data represent the active doses (expressed in µg/kg) inhibiting by 50% the urethral contractions (UP) induced by noradrenaline (NA) or by hypogastric-nerve stimulation (HYP), the active doses (expressed in µg/kg) in lowering diastolic blood pressure (DBP) and the ratios (DBP/UP) between the active doses (R1 and R2).

| Example | UP | | DBP | R1 | R2 |
| --- | --- | --- | --- | --- | --- |
| | $ID_{50}$ NA | $ID_{50}$ HVP | $ED_{25}$ | (DBP/ NA) | (DBP/ HYP) |
| 1 | 3.4 | | 354.5 | 101.6 | |
| 3 | 1.3 | 2.4 | 514.7 | 396 | 214 |
| 5 | 2.7 | 3.4 | 197 | 73 | 58 |
| 6 | 2.4 | 4.5 | 196.7 | 82 | 44 |
| Prazosin* | 3.6 | 10 | 6.6   10 | 1.83 | 1 |
| Compound A* | 2.4 | 6.7 | 243   177 | 101.2 | 26.4 |

*Data from Leonardi et al., J. Pharmacol. Exp. Ther., 281:1272–1283, 1997.

The pharmacological results confirm that the compounds of the invention are $\alpha_1$-adrenoceptor antagonists with good selectivity for the $\alpha_1$ adrenoceptor, in particular with respect to the 5-$HT_{1A}$ receptor, and good affinity also for the $\alpha_{1L}$ subtype, as far as in vitro data are concerned.

The in vivo pharmacological results confirm the extremely high uroselectivity of the compounds of the invention and justify their possible use in the treatment of obstructive diseases of the lower urinary tract, including BPH.

Effective Amounts

The following represent guidelines to effective oral, parenteral or intravenous dose ranges for human hosts expressed in mg/kg of body weight per day, for use in obstructive disorders of the lower urinary tract:

| | |
| --- | --- |
| General | 0.001–20 |
| Preferred | 0.05–3 |
| Most preferred | 0.5–2 |

The most preferred values refer to oral dosing. Intravenous dosages should be 10 to 100 fold lower. Selective-use dosages, i. e., dosages that are active in the lower urinary tract without any substantial effect on blood pressure, depend on the particular compound employed. Generally, in the case of a compound selective in inhibiting urethral contraction, up to four times the amount of the $ED_{50}$ used in inhibiting urethral contraction can be administered without any substantial effect on blood pressure. Further refinements and optimisation of dosages are possible using simple routine experiments. The active compounds of the invention may be orally administered, for example, with an inert diluent or with an edible carrier, or they may be enclosed in gelatine capsules, or they may be compressed into tablets. For the purpose of oral therapeutic administration, the active compounds of the invention may be incorporated with excipients and used in the form of tablets, troches, capsules, elixirs, suspensions, syrups, wafers, chewing gum and the like. These preparations should contain at least 0.5% of active compounds, but the amount of active ingredient may be varied depending upon the particular form and may conveniently be between 5% and about 70% of the weight of the unit. The amount of active compound in such compositions is such that a suitable dosage will be obtained although the desired dosage can be obtained by administering a plurality of dosage forms. The preferred compositions and preparations according to the invention are prepared so that an oral dosage unit form contains between 1.0 and 300 milligrams of active compound. The tablets, pills, capsules, troches and the like may also contain, for example, the following ingredients: a binder such as microcrystalline cellulose, gum tragacanth or gelatine; an excipient such as starch or lactose; a disintegrating agent such as alginic acid, sodium starch glycolate, cornstarch and the like; a lubricant such as magnesium stearate or hydrogenated castor oil; a glidant such as colloidal silicon dioxide; a sweetening agent such as sucrose or saccharin; and a flavouring agent such as peppermint, methyl salicylate or orange flavoring. When the dosage unit form is a capsule, it may contain, in addition to materials of the above type, a liquid carrier such as a fatty oil. Other dosage unit forms may contain other various materials which modify the physical form of the dosage unit, for example, as coatings. Thus, tablets or pills may be coated with sugar, shellac or other enteric coating agents. A syrup may contain, in addition to the active compounds, sucrose as a sweetening agent and certain preservatives, dyes, coloring and flavors. The materials used in preparing these various compositions should be pharmaceutically pure and nontoxic in the amounts used. For the purpose of parenteral therapeutic administration, the active compounds of the invention may be incorporated into a solution or suspension. These preparations should contain at least 0.1% of active compound, but this may be varied between 0.5 and about 30% of the weight thereof. The amount of active compound in such compositions is such that a suitable dosage will be obtained. The preferred compositions and preparations according to the present inventions are prepared so that a parenteral dosage unit contains between 0.2 and 100 milligrams of active compound. The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulphite; chelating agents such as ethylenediaminetetraacetic acid; buffers such as acetates; citrates or phosphates and agents for the adjustment of tonicity such as sodium chloride or dextrose. The parenteral multiple-dose vials may be of glass or plastics material. The frequency of administration of the present compounds and compositions may be adjusted based on need and physician's advice but will typically be once or twice a day. The duration of treatment will be while symptoms persist, even indefinitely.

Additional compositions suitable for administration by various routes and containing compounds according to the present invention are also within the scope of the invention. Dosage forms, additional ingredients and routes of administration contemplated herein include those disclosed in the U.S. Pat. No. 4,089,969, Muchowski et al. and U.S. Pat. No. 5,091,182, Ong et al., both incorporated by reference in their entirety.

All U.S. patents and other references listed herein are hereby incorporated by reference. In case of conflict in definitions, the present disclosure controls.

What is claimed is:

1. A compound having the formula:

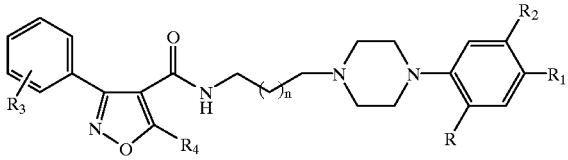

wherein
R is selected from the group consisting of alkyl, alkoxy, polyfluoroalkoxy, hydroxy and trifluoromethanesulfonyloxy group,
each of $R_1$ and $R_2$ is independently selected from the group consisting of hydrogen, halogen, polyfluoroalkoxy and alkoxy group,
$R_3$ is one or more substituents selected from the group consisting of hydrogen, halogen, alkyl, alkoxy, nitro, amino, acylamino, cyano, alkoxycarbonyl, and carboxamido group,
$R_4$ represents a hydrogen atom or an alkyl or arylalkyl group, and
n is 0, 1 or 2, or
an N-oxide thereof or a pharmaceutically acceptable salt of any of the foregoing.

2. A compound according to claim 1 wherein R is selected from the group consisting of methyl, methoxy, 2,2,2,-trifluoroethoxy, hydroxy and trifluoromethanesulfonyloxy.

3. A compound according to claim 1 wherein $R_1$ is selected from the group consisting of hydrogen and fluorine.

4. A compound according to claim 1 wherein $R_2$ is selected from the group consisting of hydrogen, chlorine and 2,2,2-trifluoroethoxy.

5. A compound according to claim 1 wherein $R_3$ is carboxamido.

6. A compound according to claim 1 wherein $R_4$ is selected from the group consisting of methyl, ethyl, 2-phenylethyl, 3-phenylpropyl and hydrogen.

7. A compound according to claim 1 wherein n=1.

8. A compound selected from the group consisting of

N-{3-[4-(5-Chloro-2-methoxyphenyl)-1-piperazinyl]propyl}-5-methyl-3-phenylisoxazole-4-carboxamide, N-{3-[4-(5-Chloro-2-hydroxyphenyl)-1-piperazinyl]propyl}-5-methyl-3-phenylisoxazole-4-carboxamide, 5-Methyl-3-phenyl-N-{3-[4-[2-(2,2,2-trifluoroethoxy)phenyl]-1-piperazinyl]-propyl}isoxazole-4-carboxamide, N-{3-[4-[2-Methoxy-5-(2,2,2-trifluoroethoxy)phenyl]-1-piperazinyl]propyl}-5-methyl-3-phenylisoxazole-4-carboxamide, N-{3-[4-[5-Fluoro-2(2,2,2-trifluoroethoxy)phenyl]-1-piperazinyl]propyl}-5-methyl-3-phenylisoxazole-4-carboxamide, N-{3-[4-[4-Fluoro-2(2,2,2-trifluoroethoxy)phenyl]-1-piperazinyl]propyl}-5-methyl-3-phenylisoxazole-4-carboxamide, N-{3-[4-(5-Chloro-2-trifluoromethanesulphonyloxy)-1-piperazinyl]propyl}-5-methyl-3-phenylisoxazole-4-carboxamide, 3-(4-Fluorophenyl)-N-{3-[4-[4-fluoro-2-(2,2,2-trifluoroethoxy)phenyl]-1-piperazinyl]propyl}isoxazole-4-carboxamide, 3-(2-Chloro-6-fluorophenyl)-N-{3-[4-[4-fluoro-2-(2,2,2-trifluoroethoxy)phenyl]-1-piperazinyl]propyl}-5-methylisoxazole-4-carboxamide, 3-(2,6-Dichlorophenyl)-N-{3-[4-[4-fluoro-2-(2,2,2-trifluoroethoxy)phenyl]-1-piperazinyl]propyl}-5-methylisoxazole-4-carboxamide, 3-(2-Chlorophenyl)-N-{3-[4-[4-fluoro-2-(2,2,2-trifluoroethoxy)phenyl]-1-piperazinyl]propyl}-5-methylisoxazole-4-carboxamide, 3-(2-Chloro-6-fluorophenyl)-5-methyl-N-{3-[4-[2-(2,2,2-trifluoroethoxy)phenyl]-1-piperazinyl]propyl}isoxazole-4-carboxamide, 3-(2-Chlorophenyl)-5-methyl-N-{3-[4-[2-(2,2,2-trifluoroethoxy)phenyl]-1-piperazinyl]propyl}isoxazole-4-carboxamide, 3-(2,6-Dichlorophenyl)-5-methyl-N-{3-[4-[2-(2,2,2-trifluoroethoxy)phenyl]-1-piperazinyl]propyl}isoxazole-4-carboxamide, N-{3-[4-[4-Fluoro-2-(2,2,2-trifluoroethoxy)phenyl]-1-piperazinyl]propyl}-3-phenyl-isoxazole-4-carboxamide, 3-(4-Fluorophenyl)-N-{3-[4-[2-(2,2,2-trifluoroethoxy)phenyl]-1-piperazinyl]propyl}isoxazole-4-carboxamide, 3-Phenyl-N-{3-[4-[2-(2,2,2-trifluoroethoxy)phenyl]-1-piperazinyl]propyl}isoxazole-4-carboxamide, 3-(4-Fluorophenyl)-N-{3-[4-[4-fluoro-2-(2,2,2-trifluoroethoxy)phenyl]-1-piperazinyl]propyl}-5-methylisoxazole-4-carboxamide, 5-Ethyl-3-phenyl-N-{3-[4-[2-(2,2,2-trifluoroethoxy)phenyl]-1-piperazinyl]propyl}isoxazole-4-carboxamide, 5-Ethyl-N-{3-[4-[4-fluoro-2-(2,2,2-trifluoroethoxy)phenyl]-1-piperazinyl]propyl}-3-phenylisoxazole-4-carboxamide, 3-(4-Fluorophenyl)-5-methyl-N-{3-[4-[2-(2,2,2-trifluoroethoxy)phenyl]-1-piperazinyl]propyl}isoxazole-4-carboxamide, 3-(2-Fluorophenyl)-N-{3-[4-[4-fluoro-2-(2,2,2-trifluoroethoxy)phenyl]-1-piperazinyl]propyl}-5-methylisoxazole-4-carboxamide, 3-(2-Fluorophenyl)-5-methyl-N-{3-[4-[2-(2,2,2-trifluoroethoxy)phenyl]-1-piperazinyl]propyl}isoxazole-4-carboxamide, 3-(3-Fluorophenyl)-N-{3-[4-[4-fluoro-2-(2,2,2-trifluoroethoxy)phenyl]-1-piperazinyl]propyl}-5-methylisoxazole-4-carboxamide, 3-(3-Fluorophenyl)-5-methyl-N-{3-[4-[2-(2,2,2-trifluoroethoxy)phenyl]-1-piperazinyl]propyl}isoxazole-4-carboxamide, 3-4(-Methoxyphenyl)-5-methyl-N-[3-[4-[2-(2,2,2-trifluoroethoxy)phenyl]-1piperazinyl]propyl]isoxazole-4-carboxamide, N-{3-[4-[4-Fluoro-2-(2,2,2-trifluoroethoxy)phenyl]-1-piperazinyl]propyl]-3-(4-methoxyphenyl)-5-methylisoxazole-4-carboxamide, N-{3-[4-4-Fluoro-2(2,2,2-trifluoroethoxy)phenyl]-1-piperazinyl]propyl}-3-phenyl-5-(2-phenylethyl)isoxazole-4-carboxamide, N-{3-[4-[4-Fluoro-2-(2,2,2-trifluoroethoxy)phenyl]-1-piperazinyl]propyl}-3-phenyl-5-(3-phenylpropyl)isoxazole-4-carboxamide, N-{3-[4-[4-Fluoro-2-methoxyphenyl]-1-piperazinyl]propyl}-5-methyl-3-phenylisoxazole-4-carboxamide, N-{3-[4-(4-Fluoro-2-methylphenyl)-1-piperazinyl]propyl}-5-methyl-3-phenylisoxazole-4-carboxamide, N-{3-[4-(4-Chloro-2-methylphenyl)-1-piperazinyl]propyl}-5-methyl-3-phenylisoxazole-4-carboxamide, N-{3-[4-[4-Fluoro-2-(1methylethoxy)phenyl]-1-piperazinyl]propyl}-5-methyl-3-phenylisoxazole-4-carboxamide, N-[3-[4-(4-Chloro-2-methoxyphenyl)-1-piperazinyl]propyl]-5-methyl-3-phenylisoxazole-4-carboxamide,
N-[3-[4-[4-Chloro-2-(2-methylethoxy)phenyl]-1-piperazinyl]propyl]-5-methyl-3-phenylisoxazole-4-carboxamide, and
N-[3-[4-(2-Ethoxy-4-fluoro)-1-piperazinyl]propyl]-5-methyl-3-phenylisoxazole-4-carboxamide, or an N-oxide or a pharmaceutically acceptable salt of any of the foregoing compound.

9. A pharmaceutical composition comprising a compound according to claim 1 and a pharmaceutically acceptable diluent or carrier.

10. A pharmaceutical composition comprising a compound according to claim 8 and a pharmaceutically acceptable diluent or carrier.

11. A process for producing a compound according to claim 1 comprising the step of condensing 3-arylisoxazole-4-carboxylic acid or an ester, amide, or anhydride of 3-arylisoxazole-4-carboxylic acid with an N-(ω-aminoalkyl)-N'-phenylpiperazine compound of formula 2

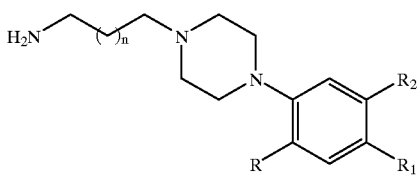

2 wherein
R is selected from the group consisting of alkoxy, polyfluoroalkoxy, alkyl, hydroxy and trifluoromethanesulfonyloxy,
each of $R_1$ and $R_2$ independently is selected from the group consisting of hydrogen, halogen, polyfluoroalkoxy and alkoxy,
and n=0, 1 or 2.

12. A process according to claim 11, wherein said condensing step is carried out in the presence of a condensing agent selected from the group consisting of dicyclohexylcarbodiimide and diethyl cyanophosphonate.

13. A process according to claim 12 wherein said condensing step is carried out in the presence of a promoting agent selected from the group consisting of N-hydroxysuccinimide, 4-dimethylaminopyridine and N,N'-carbonyldiimidazole.

14. A process according to claim 11 wherein said condensation is carried out in a solvent selected from the group consisting of aprotic and chlorinated solvents.

15. A process according to claim 14 wherein said solvent is selected from the group consisting of dimethylformamide and chloroform.

16. A process according to claim 11 wherein said condensation step is carried out at a temperature of between about −10 and 140° C.

17. A process for producing a compound according to claim 1 comprising the steps of condensing 3-arylisoxazole-4-carboxylic acid or an ester, amide, or anhydride of 3-arylisoxazole-4-carboxylic acid with an amine of formula

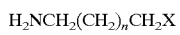

wherein n=0, 1 or 2 and X is selected from the group consisting of hydroxy, halogen, alkylsulphonyloxy, and arylsulphonyloxy to form the compound of formula 3

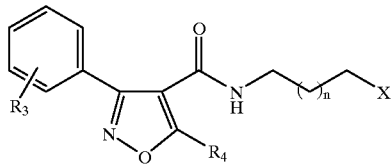

3 and reacting the compound of the formula 3 with a phenylpiperazine compound of fomula 4

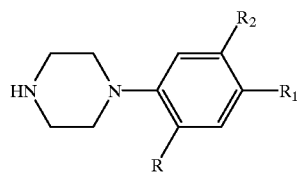

4 wherein
R is selected from the group consisting of alkoxy, polyfluoroalkoxy, alkyl, hydroxy and trifluoromethanesulphonyloxy,
each of $R_1$ and $R_2$ is independently selected from the group consistng of hydrogen, halogen, polyfluoroalkoxy and alkoxy,
with the proviso that when X in formula 3 is hydroxy it is converted into a leaving group selected from the group consisting of halogen, alkylsulphonyloxy and arylsulphonyloxy prior to reacting said compound of formula 3 with said phenylpiperazine compound of formula 4.

18. A process according to claim 17 wherein said condensation step is carried out in the presence of a condensing agent selected from the group consisting of dicyclohexylcarbodiimide and diethyl cyanophosphonate.

19. A process according to claim 18 wherein said condensation step is carried out in the presence of a catalyst selected from the group consisting of N-hydroxysuccinimide, 4-dimethylaminopyridine and N,N'-carbonyldiimidazole.

20. A process according to claim 17 wherein said condensation step is carried out in the absence of a solvent.

21. A process according to claim 17 wherein said condensation step is carried out in the presence of a solvent selected from the group consisting of aprotic and chlorinated solvents.

22. A process according to claim 21 wherein said solvent is selected from the group consisting of dimethylformamide and chloroform.

23. A process according to claim 17 wherein said condensation step is performed at a temperature within the range of about 10 to about 140° C.

24. A process accordiog to claim 17 wherein the reaction of said compound of formula 3 and said phenylpiperazine compound of formula 4 is performed in the presence of a base.

25. The process of claim 24 wherein said base is potassium carbonate.

26. A process according to claim 17 wherein the reaction of said compound of formula 3 and said phenylpiperazine derivative 4 is performed in the absence of a solvent.

27. A process according to claim 17 wherein the reaction of said compound of formula 3 and said phenylpiperazine derivative 4 is performed in a polar solvent.

28. A process according to claim 17 wherein the reaction of said compound of formula 3 and said phenylpiperazine derivative 4 is performed at a temperature within the range of about 20 to about 200° C.

29. A method for treating contractions of the urethra and lower urinary tract, the method comprising administering a compound according to claim 1 to a mammal in need of such treatment in an amount effective for treating said contractions.

30. The method according to claim 29 wherein the administration of said compound causes limited effects on the blood pressure of said mammal.

31. A method for treating contractions of the urethra and lower urinary tract, the method comprising administering a compound according to claim 8 to a mammal in need of such treatment in an amount effective for treating said contractions.

32. The method according to claim 31 wherein the administration of said compound causes limited effects on the blood pressure of said mammal.

33. A method for treating diseases associated with overactivity of an $\alpha_1$ adrenergic receptor, which diseases are treated by reducing said overactivity, the method comprising exposing said receptor to an effective amount of a compound according to claim 1, thereby blocking said receptor and lowering the activity of said receptor.

34. A method according to claim 33 in which exposing said receptor comprises administering the compound to a mammal possessing said receptor.

35. A method for treating diseases associated with overactivity of an $\alpha_1$ adrenergic receptor, which diseases are treated by reducing said overactivity, the method comprising exposing said receptor to an effective amount of a compound according to claim 8, thereby blocking said receptor and lowering the activity of said receptor.

36. A method according to claim 35 in which exposing said receptor comprises administering the compound to a mammal possessing said receptor.

37. A method for the treatment of a patient suffering from benign prostatic hyperplasia, the method comprising administering an effective amount of a compound according to claim 1 to a patient in need of such treatment.

38. A method for the treatment of a patient suffering from benign prostatic hyperplasia, the method comprising administering an effective amount of a compound according to claim 8 to a patient in need of such treatment.

39. A method for the treatment of a patient suffering from excessive intraocular pressure, the method comprising administering an effective amount of a compound according to claim 1 to a patient in need of such treatment.

40. A method for the treatment of a patient suffering from excessive intraocular pressure, the method comprising administering an effective amount of a compound according to claim 8 to a patient in need of such treatment.

41. A method for the treatment of a patient suffering from cardiac arrhythmia, the method comprising administering an effective amount of a compound according to claim 1 to a patient in need of such treatment.

42. A method for the treatment of a patient suffering from cardiac arrhythmia, the method comprising administering an effective amount of a compound according to claim 8 to a patient in need of such treatment.

43. A method for the treatment of a patient suffering from erectile dysfunction, the method comprising administering an effective amount of a compound according to claim 1 to a patient in need of such treatment.

44. A method for the treatment of a patient suffering from erectile dysfunction, the method comprising administering an effective amount of a compound according to claim 8 to a patient in need of such treatment.

45. A method for the treatment of a patient suffering from sexual dysfuction, the method comprising administering an effective amount of a compound according to claim 1 to a patient in need of such treatment.

46. A method for the treatment of a patient suffering from sexual dysfunction, the method comprising administering an effective amount of a compound according to claim 8 to a patient in need of such treatment.

47. A method for inhibiting cholesterol biosynthesis in a patient, the method comprising administering an effective amount of a compound according to claim 1 to a patient in need thereof.

48. A method for inhibiting cholesterol biosynthesis in a patient, the method comprising administering an effective amount of a compound according to claim 8 to a patient in need thereof.

49. A method for reducing sympathetically mediated pain in a patient, the method comprising administering an effective amount of a compound according to claim 1 to a patient in need thereof.

50. A method for reducing sympathetically mediated pain in a patient, the method comprising administering an effective amount of a compound according to claim 8 to a patient in need thereof.

51. A method for the treatment of lower urinary tract symptoms in a patient, the method comprising administering an effective amount of a compound according to claim 1 to a patient in need of such treatment.

52. The method according to claim 51 wherein said patient is a female.

53. A method for the treatment of lower urinary tract symptoms in a patient, the method comprising administering an effective amount of a compound according to claim 8 to a patient in need of such treatment.

54. The method according to claim 53 wherein said patient is a female.

55. A method for the treatment of neurogenic lower urinary tract dysfunction, the method comprising administering an effective amount of a compound according claim 1 to a patient in need of such treatment.

56. A method for the treatment of neurogenic lower urinary tract dysfunction, the method comprising administering an effective amount of a compound according to claim 8 to a patient in need of such treatment.

57. The method of claim 29 wherein said mammal is a human.

58. The method of claim 30 wherein said mammal is a human.

59. The method of claim 31 wherein said mammal is a human.

60. The method of claim 32 wherein said mammal is a human.

61. The method of claim 34 wherein said mammal is a human.

62. The method of claim 36 wherein said mammal is a human.

* * * * *

UNITED STATES PATENT AND TRADEMARK OFFICE
CERTIFICATE OF CORRECTION

PATENT NO. : 6,365,591 B1
DATED : April 2, 2002
INVENTOR(S) : Amedeo Leonardi, Gianni Motta, Carlo Riva and Elena Poggesi It is certified that error appears in the above-identified patent and that said Letters Patent is hereby corrected as shown below:

<u>Title page,</u>
Item [73], Assignee, delete "Recordati, S.A., Chemical and Pharmacueticals Company" and replace with -- Recordati, S.A., Chemical and Pharmaceutical Company --

Signed and Sealed this

Fifteenth Day of October, 2002

*Attest:*

*Attesting Officer*

JAMES E. ROGAN
*Director of the United States Patent and Trademark Office*